United States Patent
Tsuchiya

(10) Patent No.: US 6,704,110 B2
(45) Date of Patent: Mar. 9, 2004

(54) METHOD AND APPARATUS FOR MEASURING INTERNAL INFORMATION OF SCATTERING MEDIUM

(75) Inventor: Yutaka Tsuchiya, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 408 days.

(21) Appl. No.: 09/848,252

(22) Filed: May 4, 2001

(65) Prior Publication Data

US 2001/0038454 A1 Nov. 8, 2001

Related U.S. Application Data

(63) Continuation-in-part of application No. PCT/JP99/06181, filed on Nov. 5, 1999.

(30) Foreign Application Priority Data

Nov. 5, 1998 (JP) ............................................. 10-314613

(51) Int. Cl.[7] ............................ G01N 21/00; A61B 5/00
(52) U.S. Cl. ........................ 356/432; 356/434; 356/441; 356/442; 600/310; 600/322
(58) Field of Search ........................ 356/39–42, 432, 356/434, 441, 442; 600/310, 322, 323, 324, 344, 473, 476, 479

(56) References Cited

U.S. PATENT DOCUMENTS

| | | | |
|---|---|---|---|
| 5,694,931 A | * 12/1997 | Tsuchiya | 600/310 |
| 5,713,352 A | 2/1998 | Essenpreis et al. | 128/633 |
| 5,792,051 A | 8/1998 | Chance | 600/310 |
| 6,233,470 B1 | * 5/2001 | Tsuchiya | 600/310 |
| 6,236,871 B1 | * 5/2001 | Tsuchiya | 600/310 |
| 6,240,305 B1 | * 5/2001 | Tsuchiya | 600/310 |
| 6,335,792 B1 | * 1/2002 | Tsuchiya | 356/432 |

FOREIGN PATENT DOCUMENTS

| | | |
|---|---|---|
| EP | 0 826 958 A2 | 3/1998 |
| EP | 0 834 277 A1 | 4/1998 |
| JP | 07-163571 | 6/1995 |
| JP | 08-094517 | 4/1996 |
| JP | 09-061343 | 3/1997 |
| JP | 10-073481 | 3/1998 |
| JP | 10-111238 | 4/1998 |
| WO | WO 98/34097 | 8/1998 |

OTHER PUBLICATIONS

"Quantitation of Absorbers in Turbid Media Using Time–Integrated Spectroscopy Based on Microscopic Beer–Lambert Law," Japanese Journal of Applied Physics, Part 1, vol. 37, No. 5A, pp. 2724–2727, May 15, 1998, Hedong Zhang et al.

* cited by examiner

*Primary Examiner*—Russell Adams
*Assistant Examiner*—Andrew Seuer
(74) *Attorney, Agent, or Firm*—Morgan, Lewis & Bockius LLP

(57) ABSTRACT

Pulsed light of predetermined wavelengths or modulated light of predetermined frequencies from a light source 5 is injected into a scattering medium 1 as a measured object and output light therefrom is detected by a photodetector 7. Further, measuring methods and apparatus are configured so as to process and compute internal information by a signal processing unit 8 and an computation processing unit 9, and the internal information of the scattering medium 1 is obtained by calculating the difference between absorption coefficients by use of the time integrated spectroscopy (TIS method) and the phase modulation spectroscopy (PMS method) based on the MBL law in accordance with a spectroscopy method (MVS method) making use of a mean pathlength and a variance, or physical quantities equivalent thereto. This enables the internal information of the scattering medium to be measured accurately and quickly.

22 Claims, 9 Drawing Sheets

METHOD AND APPARATUS FOR MEASURING INTERNAL INFORMATION OF SCATTERING MEDIUM

RELATED APPLICATION

This is a continuation-in-part application of application Ser. No. PCT/JP99/06181 filed on Nov. 5, 1999, now pending.

BACKGROUND OF THE INVENTION

1. Field of the Invention

The present invention relates to methods and apparatus for measuring internal information of scattering media, e.g., an absorption coefficient or a concentration of an absorber.

2. Related Background Art

Methods of measuring an absorption coefficient of a scattering medium being a medium to be measured, a concentration of an absorber or the like, based on the Microscopic Beer-Lambert Law (hereinafter referred to as "MBL law"), include, for example, the methods disclosed in Japanese Patent Applications Laid-Open No. H08-94517, No. H10-73481, and No. H10-111238 by the inventors. These methods based on the MBL law possess the significant feature of being theoretically free of the influence of ① the shape of medium, ② boundary conditions, ③ scattering, and so on, and the same analytical formulas can be applied to media having any medium shape, any boundary conditions, and various scattering characteristics as long as there is no reentry of photon into the scattering medium.

The measuring methods based on the MBL law can be roughly classified under four types at present. They are (1) Time Resolved Spectroscopy (hereinafter referred to as "TRS method") making use of the time-resolved profile of re-emission, (2) Time Integrated Spectroscopy (hereinafter referred to as "TIS method") making use of the time integral value of the time-resolved profile of re-emission and the mean pathlength, (3) Time Gating Spectroscopy (hereinafter referred to as "TGS method") making use of portions cut out of the time-resolved profile by gates, and (4) Phase Modulation Spectroscopy (hereinafter referred to as "PMS method") making use of modulated light. Among these, (2) the TIS method and (4) the PMS method utilizing all re-emission are advantageous from the viewpoint that optical attenuation due to scattering is great in living tissues and it is thus important to use as much re-emission as possible in practical use. These two measuring methods are in the relation of Fourier transform with each other.

SUMMARY OF THE INVENTION

While the measuring methods based on the MBL law have the many advantages as described above, the measurement accuracy thereof, however, is not sufficient yet for utilization and application in the wide range. For example, there was the problem that, in the case of a living tissue being a measured object, various individual differences, such as color of skin, presence/absence of hair, etc., affected the absolute value of light intensity or the like, so as to be the cause of degradation of the measurement accuracy. Further, the wavelength dependence of scattering coefficient also degrades the measurement accuracy.

There was another problem that reduction was insufficient in the computation time of analysis during measurement and it was thus difficult to implement real-time measurement.

The present invention has been accomplished in view of the above problems and an object of the invention is to provide measuring methods and apparatus of internal information of scattering medium capable of measurement with higher accuracy and at higher speed, when compared with the conventional measuring methods based on the MBL law.

The inventor has conducted intensive and extensive research in order to accomplish the above object and finally found that it became feasible to implement highly accurate measurement by measuring the mean pathlength and variance, particularly, for pulsed light of a plurality of different wavelength components, by the Mean and Variance based Spectroscopy (hereinafter referred to as "MVS method") utilizing the mean pathlength and variance, or physical quantities equivalent thereto, without use of information such as absolute values of light intensity or a ratio thereof, and to readily put the wavelength dependence of scattering coefficient into analytical formulas, thus accomplishing the present invention. Likewise, the inventor found that it also became feasible to implement highly accurate measurement by measuring the group delay for modulated light of a plurality of different wavelength components and the second partial derivative of logarithm of amplitude with respect to modulation frequency, thus accomplishing the present invention.

Specifically, a first measuring method of internal information of a scattering medium according to the present invention is a method comprising (1) a light injecting step of injecting pulsed light of two or more predetermined wavelengths into a scattering medium at a light injection position, (2) a light detecting step of detecting the light of the two or more predetermined wavelengths having propagated inside the scattering medium, at a photodetection position to acquire a photodetection signal, (3) a signal processing step of acquiring waveform data indicating a temporal change of intensity of the detected light, based on the photodetection signal, (4) a mean pathlength and variance computing step of performing an operation to compute a mean pathlength of plural photons composing the detected light, and a variance, based on the waveform data, and (5) an absorption coefficient difference calculating step of calculating a difference between absorption coefficients at the predetermined wavelengths, based on a predetermined relation holding among the mean pathlength, the variance, and the difference between the absorption coefficients at the two or more predetermined wavelengths.

A first measuring apparatus of internal information of a scattering medium according to the present invention is an apparatus comprising (1) light injecting means for injecting pulsed light of two or more predetermined wavelengths into a scattering medium at a light injection position, (2) light detecting means for detecting the light of the two or more predetermined wavelengths having propagated inside the scattering medium, at a photodetection position to acquire a photodetection signal, (3) signal processing means for acquiring waveform data indicating a temporal change of intensity of the detected light, based on the photodetection signal, (4) mean pathlength and variance computing means for performing an operation to compute a mean pathlength of plural photons composing the detected light, and a variance, based on the waveform data, and (5) absorption coefficient difference calculating means for calculating a difference between absorption coefficients at the predetermined wavelengths, based on a predetermined relation holding among the mean pathlength, the variance, and the difference between the absorption coefficients at the two or more predetermined wavelengths.

The above first method and apparatus according to the present invention are based on a TIMVS method, which is an MVS method in which the analysis is carried out in the time domain by the time integrated spectroscopy (TIS method). The TIMVS method using the mean pathlength and variance for the light of plural wavelength components in this way presents very significant advantages in practical use, including ① being not influenced by the individual differences and absolute values of intensity of incident light dependent upon wavelengths and positions, ② extremely simplifying the quantitative formula involving the wavelength dependence of scattering coefficient, ③ decreasing errors in determination of the zero point (t =0) of the time axis in the time-resolved spectroscopy, and so on, in addition to the advantages presented by the conventional measuring methods based on the MBL law.

In the method and apparatus, it also becomes feasible to greatly reduce the measurement and analysis time and implement real-time measurement, by applying the Simple Subtraction Method (SSM) developed by the inventors, which permits the mean pathlength of detected photons (the center of gravity of a time-resolved profile) and the variance to be computed at high speed by calculating the moment of the time-resolved profile with a computer. This SSM is described, for example, in Japanese Patent Application Laid-Open No. H09-61343.

A second measuring method of internal information of a scattering medium according to the present invention is a method comprising (1) a light injecting step of injecting modulated light of two or more predetermined wavelengths modulated at a predetermined frequency, into a scattering medium at a light injection position, (2) a light detecting step of detecting the light of the two or more predetermined wavelengths having propagated inside the scattering medium, at a photodetection position to acquire a photodetection signal, (3) a signal processing step of extracting a signal of the predetermined frequency component from the photodetection signal, (4) a group delay and second-partial-derivative-of-logarithm-of-amplitude computing step of computing a group delay of the signal of the predetermined frequency component and a second partial derivative of logarithm of amplitude with respect to the modulation frequency, based on the signal of the predetermined frequency component, and (5) an absorption coefficient difference calculating step of calculating a difference between absorption coefficients at the predetermined wavelengths, based on a predetermined relation holding among the group delay, the second partial derivative of logarithm of amplitude with respect to the modulation frequency, and the difference between the absorption coefficients at the two or more predetermined wavelengths.

A second measuring apparatus of internal information of a scattering medium according to the present invention is an apparatus comprising (1) light injecting means for injecting modulated light of two or more predetermined wavelengths modulated at a predetermined frequency, into a scattering medium at a light injection position, (2) light detecting means for detecting the light of the two or more predetermined wavelengths having propagated inside the scattering medium, at a photodetection position to acquire a photodetection signal, (3) signal processing means for extracting a signal of the predetermined frequency component from the photodetection signal, (4) group delay and second-partial-derivative-of-logarithm-of-amplitude computing means for computing a group delay of the signal of the predetermined frequency component and a second partial derivative of logarithm of amplitude with respect to the modulation frequency, based on the signal of the predetermined frequency component, and (5) absorption coefficient difference calculating means for calculating a difference between absorption coefficients at the prescribed wavelengths, based on a predetermined relation holding among the group delay, the second partial derivative of logarithm of amplitude with respect to the modulation frequency, and the difference between the absorption coefficients at the two or more predetermined wavelengths.

The above-described second method and apparatus according to the present invention are based on a PMMVS method, which is an MVS method in which the analysis is carried out in the frequency domain by the phase modulation spectroscopy (PMS method). This PMMVS method is in the relation of Fourier transform with the TIMVS method associated with the first method and apparatus according to the present invention, and the PMMVS method using the group delay and the second partial derivative of logarithm of amplitude with respect to the modulation frequency for the light of the plural wavelengths in this way presents very significant advantages in practical use, including the aforementioned advantages ①, ② described as to the TIMVS method, and ④ decreasing errors in determination of the zero point of the phase in the phase modulation spectroscopy, and so on, in addition to the advantages provided by the conventional measuring methods based on the MBL law.

DESCRIPTION OF THE PREFERRED EMBODIMENTS

Figure 1:
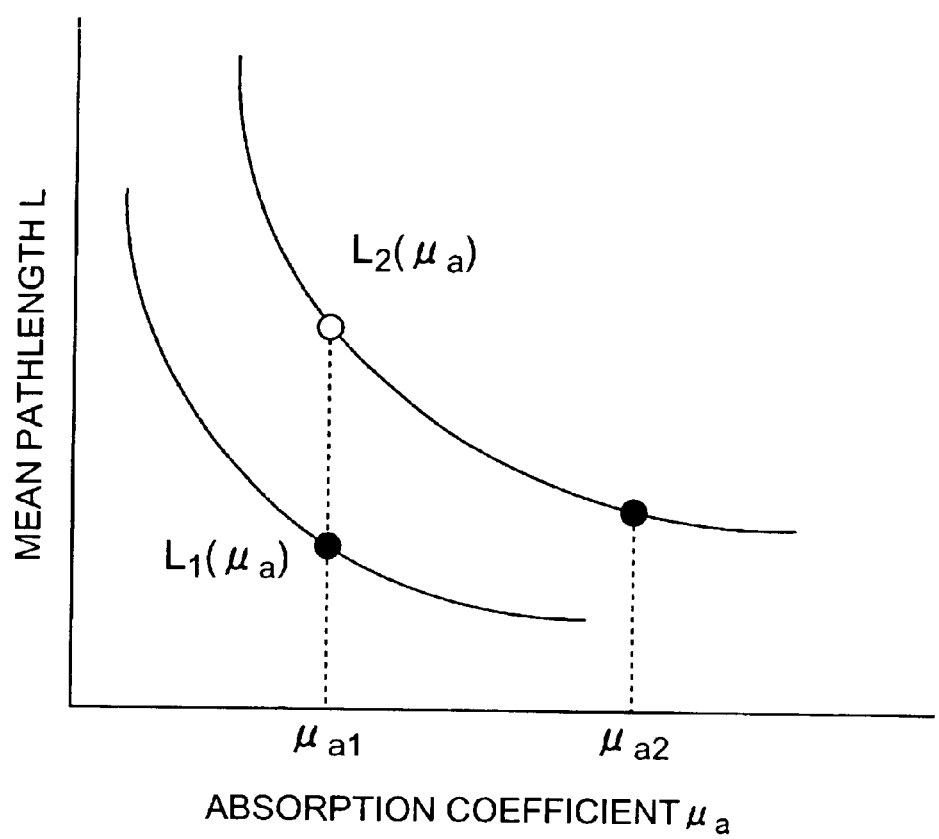
FIG. 1 is a graph to show the relationship between mean pathlength and absorption coefficient for different scattering coefficients.

Detailed below with reference to the drawings are preferred embodiments of the measuring methods and apparatus of internal information of scattering medium according to the present invention. In the description of the drawings the same elements will be denoted by the same reference symbols and redundant description will be omitted.

First, the principles of the present invention will be described.

Principles of the Invention
Calculation of absorption coefficient difference by TIS method The survival probability of photons propagating in a zigzag path inside a scattering medium is the exponential of the product of the zigzag pathlength 1 and the scattering coefficient $\mu_a$ of the medium (scattering medium), $\exp(-\mu_a 1)$. Namely, the attenuation is expressed by the product $\mu_a 1$ of the zigzag photon pathlength 1 and the absorption coefficient $\mu_a$. At this time, the impulse response h(t) of the scattering medium is a time-causal function, which is expressed as follows.

$$h(t) = h(\mu_s, \mu_a, t) = s(\mu_s, t)\exp(-\mu_a c t) \qquad (1.1a)$$

$$\frac{\partial}{\partial \mu_a}\ln h(\mu_s, \mu_a, t) = -ct = -l \qquad (1.1b)$$

$$\ln h(t) = \ln s(\mu_s, t) - \int_0^{\mu_a} l\, d\mu = \ln s(\mu_s, t) - \mu_a l \qquad (1.1c)$$

Here $\mu_s$ and $\mu_a$ represent an anisotropic scattering coefficient and an absorption coefficient, c the speed of photons in the medium, t the time of flight, and 1 the photon pathlength (distance of flight). The function $s(\mu_s, t)$ is the response at the absorption coefficient $\mu_a=0$. The time of flight t can be measured by time-resolved spectroscopy. The speed of photons c is determined by the refractive index of the scattering medium and can be deemed as a constant, for example, in the case of living tissues. The above facts are called the MBL law. A transport scattering coefficient $\mu'_s$ (also called an equivalent scattering coefficient) used hereinafter is expressed as $\mu'_s = (1-g)\mu_s$, using $\mu_s$ and an average g of cosine of scattering angles.

The temporal integration $I(\mu_s, \mu_a)$ of the impulse response h(t) of the scattering medium is given as follows.

$$I(\mu_s, \mu_a) = \int_0^\infty s(\mu_s, t)\exp(-\mu_a c t)\, dt \qquad (1.2a)$$

$$\frac{\partial \ln I(\mu_s, \mu_a)}{\partial \mu_a} = -c\frac{\int_0^\infty t s(\mu_s, t)\exp(-\mu_a c t)\, dt}{\int_0^\infty s(\mu_s, t)\exp(-\mu_a c t)\, dt} \qquad (1.2b)$$

$$= -c\langle t\rangle = -\langle l\rangle = -L(\mu_s, \mu_a)$$

$$\ln I(\mu_s, \mu_a) = -\int_0^{\mu_a} L(\mu_s, \mu)\, d\mu + \ln\int_0^\infty s(\mu_s, t)\, dt \qquad (1.2c)$$

$L(\mu_s, \mu_a) = c\langle t\rangle$ in above Eq. (1.2b) represents an average of pathlengths of detected photons (which is also called a mean pathlength). On this occasion, $\langle t\rangle$ indicates the center of gravity of the impulse response profile (mean time of flight of detected photons) and can be readily calculated by an operation with a computer (to compute the moment) from the temporal profile of the impulse response.

Next, absorption coefficient dependency of the mean pathlength $L(\mu_s, \mu_a)$ is derived as follows.

$$\frac{\partial L(\mu_s, \mu_a)}{\partial \mu_a} = -\frac{\int_0^\infty (l - \langle l\rangle)^2 s(\mu_s, t)\exp(-\mu_a c t)\, dt}{\int_0^\infty s(\mu_s, t)\exp(-\mu_a c t)\, dt} \qquad (1.3)$$

$$= -[\langle l^2\rangle - \langle l\rangle^2]$$

$$= -\sigma^2(\mu_s, \mu_a)$$

Here $\sigma^2$ represents the variance of pathlength 1, which is equivalent to a result of partially differentiating the mean pathlength $L(\mu_s, \mu_a)$ with respect to $\mu_a$ and flipping the sign, or to the second partial derivative of the temporal integration $I(\mu_s, \mu_a)$ with respect to $\mu_a$. This variance $\sigma^2(\mu_s, \mu_a)$ can be readily calculated by an operation with a computer from the temporal profile of the impulse response, similarly as in the case of the above mean pathlength $L(\mu_s, \mu_a)$.

Likewise, we can find the third partial derivative of the temporal integration $I(\mu_s, \mu_a)$ with respect to $\mu_a$, i.e., the second partial derivative of the mean pathlength $L(\mu_s, \mu_a)$ with respect to $\mu_a$, and this value provides information about profile distortion. From the mathematical aspect, if there exists the mth partial derivative, there always exist the (m-1)th and lower partial derivatives.

Here, assuming that the scattering coefficient $\mu_s$ is a constant, the Taylor expansion of the mean pathlength $L(\mu_s, \mu_a) = L(\mu_a)$ around $\mu_{a1}$ is expressed as follows.

$$L(\mu_{a1} + \delta) = L(\mu_{a1}) + \delta L'(\mu_{a1}) + \frac{1}{2!}\delta^2 L''(\mu_{a1}) + \ldots \qquad (1.4)$$

In this equation, L' and L'' represent the first and second partial derivatives of L with respect to $\mu_a$. Substituting $\delta = \mu_{a2} - \mu_{a1}$ into the above equation, we obtain the following.

$$L(\mu_{a1}) - L(\mu_{a2}) = \delta\sigma^2(\mu_{a1}) - \frac{1}{2}\delta^2 L''(\mu_{a1}) - \ldots \qquad (1.5)$$

$$\approx (\mu_{a2} - \mu_{a1})\frac{\sigma^2(\mu_{a1}) + \sigma^2(\mu_{a2})}{2}$$

This means that with the scattering coefficient being constant, a change of absorption coefficient (absorption coefficient difference), $(\mu_{a2} - \mu_{a1})$, can be calculated using the mean pathlength of the impulse response (the center of gravity of the time-resolved profile) and the variance. This novel finding will be applied to the measurement of concentration of absorber as described hereinafter.

Temporal widths of incident light pulses used in measurement are finite and bandwidths of amplifiers and counting circuits are also finite. Therefore, the temporal profile (observed waveform or observed values) obtained in actual measurement is the convolution between the impulse response of the scattering medium and the impulse response of the measuring system (also called an instrumental function).

There are two approaches below as means for determining the true mean pathlength and variance of the impulse response of the scattering medium by eliminating the influence of characteristics of the measuring apparatus from measured values. The first approach is the deconvolution method known well. This is a method of obtaining the impulse response by deconvolution of the measured values with the instrumental function and then determining the mean pathlength and variance from the resultant profile. The second approach is a method of separately determining the mean pathlength and variance in the instrumental function and the mean pathlength and variance in the observed profile and then finding the mean pathlength and variance of the impulse response of the scattering medium from these values. In this case, each of the mean pathlength and variance in the impulse response is given by a difference between corresponding values in the observed profile and in the instrumental function.

The observed profile o(t) is expressed as follows, using the impulse response (true re-emission profile) h(t) of the medium and the impulse response of the measuring system (instrumental function) i(t).

$$o(t) = i(t) \otimes h(t) \quad (2.1)$$

In the equation the symbol $\otimes$ represents the convolution operation. Let $\mu_o$, $\mu_i$, and $\mu_h$ denote centers of gravity of the profiles o(t), i(t), and h(t), respectively, and $\sigma_o^2$, $\sigma_i^2$, and $\sigma_h^2$ denote their respective variances. Let us define generating functions of the above respective profiles as follows.

$$H(s) = \int_{-\infty}^{\infty} h(t) \exp(st) dt \quad (2.2)$$

$$I(s) = \int_{-\infty}^{\infty} i(t) \exp(st) dt \quad (2.3)$$

$$O(s) = \int_{-\infty}^{\infty} o(t) \exp(st) dt \quad (2.4)$$

This definition permits these generating functions to be differentiated any times at s=0.

With these generating functions, the convolution of the profiles can be expressed by the product of the generating functions, i.e., as follows.

$$O(s) = I(s) H(s) \quad (2.5)$$

The center of gravity $\mu_o$ of o(t) is given as follows.

$$\mu_o = \frac{O'(0)}{O(0)} \quad (2.6)$$

Since the following relation is derived from Eq. (2.5):

$$O'(s) = I'(s) H(s) + I(s) H'(s) \quad (2.7),$$

we obtain the following relation therefrom.

$$\mu_o = \mu_i + \mu_h \quad (2.8)$$

Since the variance is given by the following equation:

$$\sigma^2 = \frac{O''(0)}{O(0)} - \left(\frac{O'(0)}{O(0)}\right)^2, \quad (2.9)$$

we can derive the following relation therefrom.

$$\sigma_o^2 = \sigma_i^2 + \sigma_h^2 \quad (2.10)$$

Likewise, similar relations are also attained as to the third and higher moments. Accordingly, each moment for the impulse response can be quickly calculated with a computer from the preliminarily measured instrumental function and the observed profile of the medium.

The procedures described above are the approach of determining the mean pathlength and variance of the impulse response and the absorption coefficient difference from the measured profile by the TIS method.

Calculation of Absorption Coefficient Difference by PMS Method

Next described is the measuring method using intensity-modulated light. The system function $H(\omega)$ indicating the frequency response of the medium is expressed by the Fourier transform of the impulse response h(t) as follows.

$$H(\omega) = \int_0^{\infty} h(t) \exp(-j\omega t) dt \quad (3.1)$$

$$= \int_0^{\infty} s(\mu_s, t) \exp[-(c\mu_a + j\omega)t] dt$$

$$= R(\mu_s, \mu_a, \omega) + jX(\mu_s, \mu_a, \omega)$$

$$= A(\mu_s, \mu_a, \omega) \exp[-j\phi(\mu_s, \mu_a, \omega)]$$

In this equation R and X represent the real part and imaginary part, respectively, A and $\phi$ the amplitude and phase delay, respectively, and these can be readily measured by a lock-in amplifier or the like.

Then the following relations (the Cauchy-Riemann equations) hold.

$$\frac{\partial R(\mu_s, \mu_a, \omega)}{\partial c \mu_a} = -\frac{\partial X(\mu_s, \mu_a, \omega)}{\partial \omega} \quad (3.2a)$$

$$\frac{\partial R(\mu_s, \mu_a, \omega)}{\partial \omega} = -\frac{\partial X(\mu_s, \mu_a, \omega)}{\partial c \mu_a} \quad (3.2b)$$

Thus it is seen that the system function $H(\omega)$ is a regular function. From Eqs. (3.2a) and (3.2b), we can further derive the following relations.

$$\frac{\partial \ln A(\mu_s, \mu_a, \omega)}{\partial c \mu_a} = -\frac{\partial \phi(\mu_s, \mu_a, \omega)}{\partial \omega} \quad (3.2c)$$

$$\frac{\partial \ln A(\mu_s, \mu_a, \omega)}{\partial \omega} = \frac{\partial \phi(\mu_s, \mu_a, \omega)}{\partial c \mu_a} \quad (3.2d)$$

Then we can derive the following equation, for example, from Eq. (3.2c).

$$\ln A(\mu_s, \mu_a, \omega) = -c \int_0^{\mu_a} \frac{\partial \phi(\mu_s, \mu_a, \omega)}{\partial \omega} d\mu + \ln A(\mu_s, 0, \omega) \quad (3.3)$$

This Eq. (3.3) is similar to aforementioned Eq. (1.2c) and the left side of Eq. (3.3) is observable. The integrand in the first term of the right side is the group delay and corresponds to the mean pathlength L ($\mu_s$, $\mu_a$) described previously. This group delay is approximated as follows, using the phase delays $\phi_1$ and $\phi_2$ at two modulation frequencies $\omega_1$ and $\omega_2$.

$$\frac{\partial \phi(\mu_s, \mu_a, \omega)}{\partial \omega} = \frac{\phi_2 - \phi_1}{\omega_2 - \omega_1} \quad (3.4)$$

The second term of the right side in Eq. (3.3) is a value at the absorption coefficient $\mu_a = 0$. Further, the group delay $\partial \phi(\mu_s, \mu_a, \omega)/\partial \omega$ can be approximated as follows when $\omega \ll c\mu_a$.

$$\frac{\partial \phi(\mu_s, \mu_a, \omega)}{\partial \omega} = \frac{\phi}{\omega}$$

Here $\phi/\omega$ represents the phase delay.

We can obtain the absorption coefficient dependency of the group delay as follows.

$$\frac{\partial}{\partial \mu_a} \frac{\partial \phi(\mu_s, \mu_a, \omega)}{\partial \omega} = -\frac{1}{c} \partial^2 \ln \frac{A(\mu_s, \mu_a, \omega)}{\partial \mu_a^2} \quad (3.5)$$

$$= c \frac{\partial^2 \ln A(\mu_s, \mu_a, \omega)}{\partial \omega^2}$$

Here $\partial^2 \ln A/\partial \omega^2$ in the right side of Eq. (3.5) can be readily measured using three modulation frequencies. This corresponds to the variance previously defined.

In the above discussion Eq. (3.3) to Eq. (3.5) were obtained from Eq. (3.2c), but it is also possible to obtain similar relations from Eqs. (3.2a), (3.2b), and (3.2d). The PMS method normally obviates the need for the aforementioned deconvolution operation for obtaining the true profile.

Just as in the case of the TIS method, the relation between the group delay and the change of absorption coefficient (absorption coefficient difference) is obtained as follows, assuming that the scattering coefficient $\mu_s$ is a constant.

$$\left.\frac{\partial \phi}{\partial \omega}\right|_{\mu_{a1}} - \left.\frac{\partial \phi}{\partial \omega}\right|_{\mu_{a2}} \approx \frac{c}{2}(\mu_{a2} - \mu_{a1})\left(\left.\frac{\partial^2 \ln A}{\partial \omega^2}\right|_{\mu_{a1}} + \left.\frac{\partial^2 \ln A}{\partial \omega^2}\right|_{\mu_{a2}}\right) \quad (3.6)$$

Accordingly, it is also feasible to calculate the change of absorption coefficient (absorption coefficient difference) with the scattering coefficient being constant, from actually measured values of the group delay and the absorption coefficient dependency by the PMS method, similarly as in the case of the aforementioned TIS method.

Calculation of Absorber Concentration by MVS Method

Next described is the mean and variance based spectroscopy (MVS method) to quantify the absorber concentration from values of the mean pathlength and variance of the impulse response. In the following, the transport scattering coefficient $\mu'_s(=(1-g)\mu_s)$, which is easier to measure in general, is used instead of the scattering coefficient $\mu_s$. For easier description, we will consider dual-wavelength spectroscopy of a scattering medium containing one absorber component and the principal component of water, the wavelengths used in the measurement are $\lambda_1$ and $\lambda_2$, and the optical constants at the respective wavelengths will be accompanied by subscripts 1 and 2, respectively. At this time, the following relations hold between the concentration C of the absorber and the absorption coefficients $\mu_{a1}$ and $\mu_{a2}$ of the medium at the wavelengths $\lambda_1$ and $\lambda_2$.

$$\mu_{a1} = C\varepsilon_1 + \mu_{w1}, \quad \mu_{a2} = C\varepsilon_2 + \mu_{w2} \quad (4.1a)$$

$$C = \frac{1}{\varepsilon_2 - \varepsilon_1}[(\mu_{a2} - \mu_{a1}) - (\mu_{w2} - \mu_{w1})] \quad (4.1b)$$

Here $\varepsilon_1$ and $\varepsilon_2$ indicate extinction coefficients (or absorption coefficients) for unit concentration of the absorber at the wavelengths $\lambda_1$ and $\lambda_2$, which are, for example, molar extinction coefficients for example, and $\lambda_{w1}$ and $\lambda_{w2}$ represent absorption coefficients of water at the wavelengths $\lambda_1$ and $\lambda_2$. Therefore, it is possible to quantify the concentration C of the absorber by obtaining the difference $(\mu_{a2}-\mu_{a1})$ between the absorption coefficients from measured profiles.

In execution of the above spectroscopy, ordinary media demonstrate different values of scattering coefficients at the two wavelengths ($\lambda_1$ and $\lambda_2$). Then this difference between the scattering coefficients complicates the algorithm for quantification of the absorber concentration. In the following we will first find a relation between the mean pathlength and the transport scattering coefficient and then explain a new method of quantifying the absorber concentration by use of the relation.

According to the photon diffusion equation, the mean pathlength $L(\mu'_s, \mu_a)$ in the case of reflection measurement, which will be simply abbreviated as $L_\rho$, is expressed as follows.

$$L\rho = \frac{3\mu'_s}{2} \frac{r^2}{1 + \rho\mu_{eff}} \quad (4.2a)$$

$$\mu_{eff} = (3\mu'_s\mu_a)^{1/2} \quad (4.2b)$$

The symbol $\rho$ indicates the source-detector distance, the distance between a light injection position and a photodetection position.

Now let us consider a ratio of mean pathlengths in a case wherein the absorption coefficients are equal, $\mu_a$, but the transport scattering coefficients are $\mu'_{s1}$ and $\mu'_{s2}$ (which are equal just to the transport scattering coefficients at the wavelengths $\lambda_1$ and $\lambda_2$) (though this will not usually occur). The ratio is given as follows.

$$\frac{L\rho(\mu_{s2}, \mu_a)}{L\rho(\mu_{s1}, \mu_a)} = \frac{\mu'_{s2}}{1 + \rho\mu_{eff2}} 1 + \frac{\rho\mu_{eff1}}{\mu'_{s1}} \quad (4.3)$$

Here $\mu_{eff}$ represents an effective attenuation coefficient and is given as follows.

$$\mu_{eff1} = (3\mu'_{s1}\mu_a)^{1/2}, \quad \mu_{eff2} = (3\mu'_{s2}\mu_a)^{1/2} \quad (4.4)$$

However, a photon diffusion constant independent of the absorption coefficient was used herein. When the measurement conditions are ordinary conditions, i.e., $\rho > 20$ mm, $\mu'_s > 0.8$ mm, and $\mu_a >> 0.001$ mm$^{-1}$, Eq. (4.3) is approximated as follows.

$$\frac{L\rho(\mu_{s2}, \mu_a)}{L\rho(\mu_{s1}, \mu_a)} = \left(\frac{\mu'_{s2}}{\mu'_{s1}}\right)^{1/2} \quad (4.5)$$

Namely, the ratio of mean pathlengths in the case wherein the absorption coefficients are equal but the transport scattering coefficients are different is a constant determined by a ratio of the transport scattering coefficients, independent of the absorption coefficients. Since in the measurement of actual media change of the transport scattering coefficient with change of wavelength normally also varies the absorption coefficient, it is difficult to directly measure the ratio of $L_\rho$ represented by Eq. (4.3).

The approximation of Eq. (4.5) also holds similarly for the ratio of mean pathlengths under almost equal conditions to the above, i.e., in the case of ordinary transmission measurement. FIG. 1 schematically shows by $L_1$ and $L_2$, an example of the relation between the mean pathlength L and the absorption coefficient $\mu_a$ for different transport scattering coefficients.

Eq. (4.5) above is the relation obtained based on the photon diffusion approximation, but the validity of this relation for actual media was proved by the Monte Carlo calculation to simulate scattering media and by experiments with a tissue-like phantom.

To generalize the above, the ratio of mean pathlengths at the wavelengths $\lambda_1$ and $\lambda_2$ is approximated as follows and defined by k'.

$$\frac{L_2(\mu_a)}{L_1(\mu_a)} \equiv \frac{L(\mu_{s2},\mu_a)}{L(\mu_{s1},\mu_a)} = \left(\frac{\mu'_{s2}}{\mu'_{s1}}\right)^{1/2} \equiv k' \quad (4.6)$$

$L_1(\mu_a)$ and $L_2(\mu_a)$ used herein indicate the mean pathlengths for a medium having different transport scattering coefficients but an absorption coefficient of an equal value $\mu_a$. Accordingly, use of the coefficient k' defined here permits the ratio of mean pathlengths to be estimated for the medium having the absorption coefficient of the equal value $\mu_a$ and the different transport scattering coefficients (see FIG. 2). Moreover, since the fact that Eq. (4.6) holds means that curves representing the mean pathlengths, k'×$L_1(\mu_a)$ and $L_2(\mu_a)$, are laid on each other on the plane ($\mu_a$,L), the following relation holds for the variances $\sigma^2 1$ ($\mu'_{s1}, \mu_a$) and $\sigma^2(\mu'_{s2}, \mu_a)$ at $\mu_a$ of the curves $L_1(\mu_a)$ and $L_2(\mu_a)$ indicating the mean pathlengths.

$$\sigma^2(\mu'_{s2}, \mu_a) = \sigma_2^2(\mu_a) = k'\sigma^2(\mu'_{s1}, \mu_a) = k'\sigma_1^2(\mu_a) \quad (4.7)$$

The above knowledge is very significant in the following sense. Namely, use of the coefficient k' defined in Eq. (4.6) permits us to normalize the mean pathlength $L(\mu'_s, \mu_a)$ for media with different transport scattering coefficients. As a consequence, we can unitarily handle the mean pathlengths for the media with different transport scattering coefficients.

Now let us describe how to determine the concentration C of the absorber, using this relation.

The introduction of the coefficient k' as described above reduces the spectroscopy of the media exhibiting the wavelength dependence of the transport scattering coefficient to measurement of concentration of absorber with the transport scattering coefficient being constant. As a result, we need only to consider one curve indicating the mean pathlength on the plane ($\mu_a$,L) and can apply Eq. (1.5) to the measurement of absorber concentration. Now, referring to Eq. (1.5) with use of the mean pathlength $L_2=k'L_1$ normalized by k', the following relation holds as to the difference between absorption coefficients.

$$L_2(\mu_{a1}) - L_2(\mu_{a2}) = (\mu_{a2} - \mu_{a1}) \frac{\sigma_2^2(\mu_{a1}) + \sigma_2^2(\mu_{a2})}{2}$$

Since there are the following relations:

$$L_2(\mu_{a1}) = L(\mu'_{s2}, \mu_{a1}) = k'L(\mu'_{s1}, \mu_{a1}) = k'L_1(\mu_{a1})$$

$$\sigma_2^2(\mu_{a1}) = \sigma^2(\mu'_{s2}, \mu_{a1}) = k'\sigma^2L(\mu'_{s1}, \mu_{a1}) = k'\sigma_1^2(\mu_{a1})$$

the following relation finally holds.

$$k'L_1(\mu_{a1}) - L_2(\mu_{a2}) = (\mu_{a2} - \mu_{a1})k'\sigma_1^2(\mu_{a1}) + \frac{\sigma_2^2(\mu_{a2})}{2} \quad (4.8)$$

This means that the absorption coefficient difference can be quantified using the mean pathlengths $L_1(\mu_{a1})$, $L_2(\mu_{a2})$ and the variances $\sigma_1^2(\mu_{a1})$, $\sigma_2^2(\mu_{a2})$, which are obtained from measured values.

From the above, the absorber concentration C is finally obtained as follows.

$$C = \frac{1}{\varepsilon_2 - \varepsilon_1}\left[\frac{2[k'L_1(\mu_{a1}) - L_2(\mu_{a2})]}{k'\sigma_1^2(\mu_{a1}) + \sigma_2^2(\mu_{a2})} - (\mu_{w2} - \mu_{w1})\right] \quad (4.9)$$

This yields the equation for quantifying the absorber concentration C by dual-wavelength spectroscopy. Since the mean pathlength term is (k'$L_1-L_2$) herein, the problem of error in determination of the zero point of the time axis (t=0) in time-resolved spectroscopy is largely relaxed in comparison with ($L_1+L_2$) in the conventional method. This effect is particularly great in the case of living tissues with $\mu'_s \approx 1$.

In the case of the phase modulation spectroscopy (PMS method), the concentration is given as follows in the same manner as above.

$$C = \frac{1}{\varepsilon_2 - \varepsilon_1}\left[\frac{2[k'\phi'_1(\mu_{a1}) - \phi'_2(\mu_{a2})]}{c[k'\ln A''_1(\mu_{a1}) + \ln A''_2(\mu_{a2})]} - (\mu_{w2} - \mu_{w1})\right] \quad (4.10)$$

However, the notation follows the following definition.

$$\varphi'_1(\mu_{a1}) = \left.\frac{\partial \phi(\mu'_{s1}, \mu_a)}{\partial \omega}\right|_{\mu_{a1}}, \quad \ln A''_1(\mu_{a1}) = \left.\frac{\partial^2 \ln A(\mu'_{s1}, \mu_a)}{\partial \omega^2}\right|_{\mu_{a1}} \quad (4.11)$$

$$\varphi'_2(\mu_{a2}) = \left.\frac{\partial \phi(\mu_{s2}, \mu_a)}{\partial \omega}\right|_{\mu_{a2}}, \quad \ln A''_2(\mu_{a2}) = \left.\frac{\partial^2 \ln A(\mu'_{s2}, \mu_a)}{\partial \omega^2}\right|_{\mu_{a2}}$$

Since the group delay term is also (k'$\phi'_1 - \phi'_2$) in above Eq. (4.10), the problem of error in determination of the zero point of the phase ($\phi=0$) in the phase modulation spectroscopy is largely relaxed in comparison with ($\phi_1+\phi_2$) in the conventional method. This effect is also particularly great in the case of the living tissues with $\mu'_s \approx 1$, as above.

It is apparent from the above that the spectroscopy (MVS method) according to the present invention with use of the mean pathlength and variance, or physical quantities equivalent thereto, presents tremendous advantages, including ① there will arise no problem from the individual differences and the absolute value of incident photon intensity dependent upon the wavelength and position, ② the quantitative equation is very simple with inclusion of the wavelength dependency of scattering coefficient, ③ the problem of error is relaxed in the determination of the zero point of the time axis (t=0) in the time-resolved spectroscopy, ④ the problem of error is relaxed in the determination of the zero point of the phase in the phase modulation spectroscopy, and so on, in addition to those of the conventional measuring methods based on the MBL law.

Eq. (4.8) above can also be derived as follows. First, the following is yielded from Eq. (1.3).

$$L(\mu'_s, \mu_{a1}) = -\int_0^{\mu_{a1}} \sigma^2(\mu_s, \mu_a)d\mu_a + L(\mu_s, 0) \quad (A.1)$$

Then the difference between mean pathlengths at the wavelengths $\lambda_1$ and $\lambda_2$ is given as follows.

$$L(\mu'_{s1}, \mu_{a1}) - L(\mu'_{s2}, \mu_{a2}) = \int_0^{\mu_{a2}} \sigma^2(\mu_{s2}, \mu_a)d\mu_a - \int_0^{\mu_{a1}} \sigma^2(\mu_{s1}, \mu_a)d\mu_a - L(\mu_{s2}, 0) + L(\mu_{s1}, 0) \quad (A.2)$$

Assuming Eq. (4.6) and Eq. (4.7), the following relation is obtained.

$$L(\mu'_{s1}, \mu_{a1}) - L(\mu'_{s2}, \mu_{a2}) = (k'-1)\int_0^{\mu_{a1}} \sigma^2(\mu_{s1}, \mu_a)d\mu_a +$$

$$\int_{\mu_{a1}}^{\mu_{a2}} \sigma^2(\mu_{s2}, \mu_a)d\mu_a -$$

$$(k'-1)L(\mu_{s1}, 0)$$

$$= -(k'-1)L(\mu'_{s1}, \mu_{a1}) +$$

$$\int_{\mu_{a1}}^{\mu_{a2}} \sigma^2(\mu_{s2}, \mu_a)d\mu_a$$

As a result, aforementioned Eq. (4.8b), i.e., the following equation is derived.

$$k'L_1(\mu_{a1}) - L_2(\mu_{a2}) = (\mu_{a2} - \mu_{a1}) \frac{k'\sigma_1^2(\mu_{a1}) + \sigma_2^2(\mu_{a2})}{2} \quad (4.8b)$$

Next described is a method of quantifying the ratio of transport scattering coefficients. The mean pathlength $L_{92}$ ($\mu'_s, \mu_a$) in the reflection measurement is given by aforementioned Eq. (4.2) and is rewritten as follows by abbreviating it as L.

$$L = \frac{3\mu'_s}{2} \frac{r^2}{1 + \rho\mu_{eff}} \quad (5.1a)$$

$$\mu_{eff} = (3\mu'_s\mu_a)^{1/2} \quad (5.1b)$$

In the equation ρ represents the source-detector distance. Thus the variance $\sigma^2$ is yielded as follows.

$$\sigma^2 = \frac{\partial^2 \ln I}{\partial \mu_a^2} = -\frac{\partial L}{\partial \mu_a} = \frac{L^2}{\rho\mu_{eff}} \quad (5.2)$$

Then we obtain the following equations for the transport scattering coefficient $\mu'_s$ and the absorption coefficient $\mu_a$, by describing them using the mean pathlength L and variance $\sigma^2$.

$$\mu_a = \frac{1}{2L\sigma^2} \frac{L^2}{\sigma^2 + L^2} \quad (5.3a)$$

$$\mu'_s\left[1 + \left(\frac{4}{3\mu'_s\rho}\right)\right] = \frac{2L}{3\rho^2}\left(1 + \frac{L^2}{\sigma^2}\right) \quad (5.3b)$$

In the ordinary measurement, i.e., when $3\mu'_s\rho >> 4$, the transport scattering coefficient can be approximated as follows.

$$\mu'_s = \frac{2L}{3\rho^2}\left(1 + \frac{L^2}{\sigma^2}\right) \quad (5.4)$$

From the above, the transport scattering coefficient $\mu'_s$ and the absorption coefficient $\mu_a$ can be quantified using the mean pathlength L and variance $\sigma^2$ computed from measured values. This method has the most significant feature and advantage of being simple and attains high accuracy for relatively large media, and the measurement accuracy of the transport scattering coefficient $\mu'_s$ and the absorption coefficient $\mu_a$ at this time is approximately 10%. However, this method presents excellent quantification accuracy for the ratio of transport scattering coefficients in measurement with different media or at different wavelengths. Namely, the transport scattering coefficient ratio can be measured with high accuracy and at high speed by the above method. In this case, the aforementioned subtraction method can be utilized for obtaining the mean pathlength L and variance $\sigma^2$.

Accordingly, the ratio of transport scattering coefficients obtained in measurement at the wavelengths $\lambda_1$ and $\lambda_2$, i.e., $\mu'_s(\lambda_2)/\mu'_s(\lambda_1)$, is given by the following equation, using the mean pathlengths L and variances $\sigma^2$ obtained in measurement at the respective wavelengths.

$$\frac{\mu'(\lambda_2)}{\mu'(\lambda_1)} \equiv \frac{\mu'_{s2}}{\mu'_{s1}} = \frac{L_2}{L_1} \frac{1 + (L_2/\sigma_2)^2}{1 + (L_1/\sigma_1)^2} \quad (5.5)$$

Therefore, aforementioned k' is given as follows.

$$k' = \left(\frac{\mu'_{s2}}{\mu'_{s1}}\right)^{1/2} = \left(\frac{L_2}{L_1} \frac{1 + (L_2/\sigma_2)^2}{1 + (L_1/\sigma_1)^2}\right)^{1/2} \quad (5.6)$$

It is, however, noted that the mean pathlengths and variances are expressed by their abbreviations.

From the above, the absorber concentration C can be determined from measured values, by substituting Eq. (5.6) into Eq. (4.8). If the ratio of transport scattering coefficients is known, this known value may also be used. This ratio of transport scattering coefficients may also be gained by another method.

Preferred embodiments of the measuring methods and apparatus based on the above-stated measurement principles will be described below in detail.

First Embodiment

Figure 2:
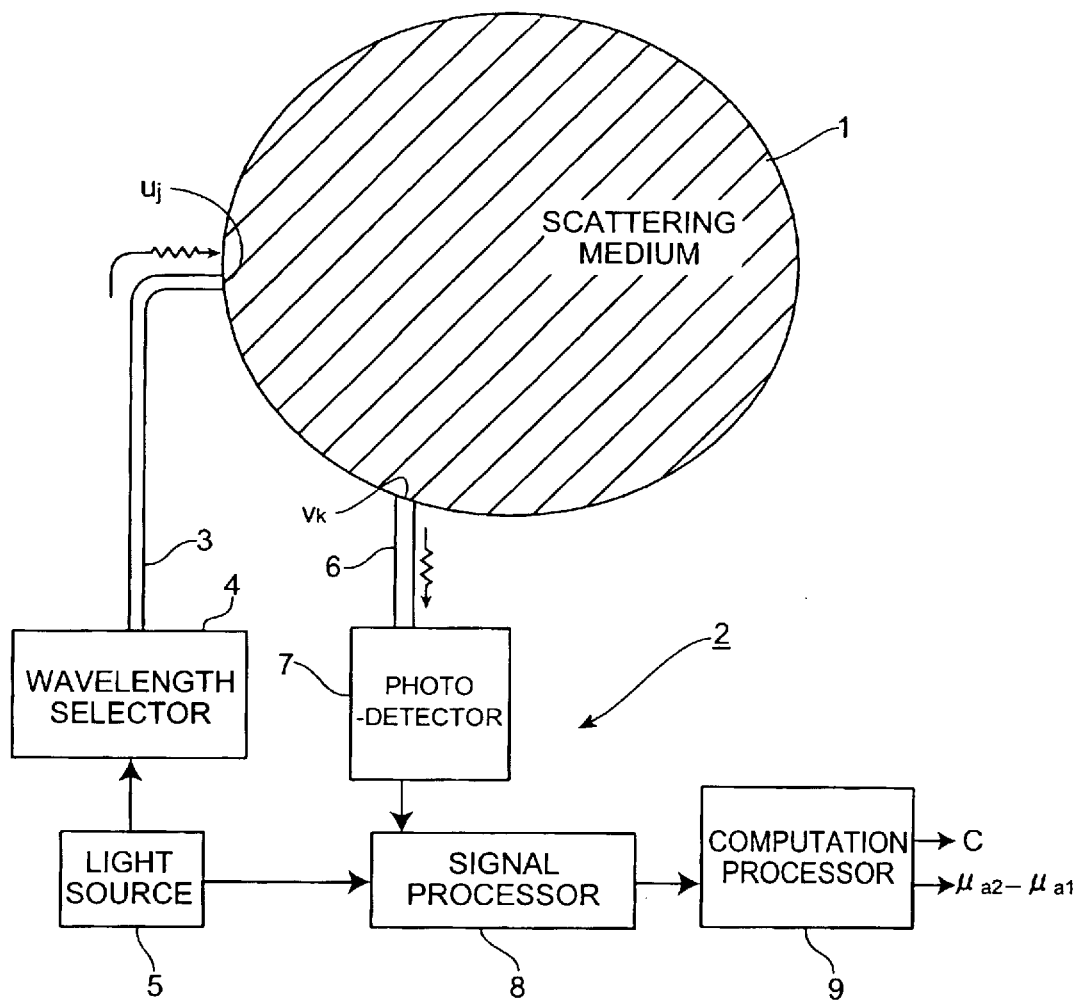
FIG. 2 is a schematic diagram to show an embodiment of the measuring apparatus of internal information of scattering medium according to the present invention.

The first embodiment as a preferred embodiment of the present invention will be described with reference to FIG. 2 to FIG. 4. FIG. 2 shows a measuring system according to the present invention to quantify the concentration C of an absorber in a scattering medium 1, using light of two wavelengths. For simplicity of description, let us consider a liquid medium containing one absorber, in which the scattering and absorption characteristics are uniform. The liquid is, for example, water and it is necessary to take absorption of water in the measurement into consideration.

The apparatus illustrated in FIG. 2 is provided with a light guide 3 for injection of light and an output end of the light guide 3 is located at a predetermined position on the surface of the scattering medium 1. A light source 5 is optically coupled through a wavelength selector 4 to an input end of the light guide 3 and pulsed light emitted from the light source 5 is subjected to wavelength selection to the predetermined wavelength $\lambda_1$ and/or $\lambda_2$ in the wavelength selector 4. The light is then guided through the light guide 3 to be injected at the position $u_j$ into the scattering medium 1.

The time width of this pulsed light can be set to any value short enough to derive the mean pathlength of the impulse response from a photodetection signal and is normally selected in the range of approximately 10 ps to 1 ns. The wavelengths of the light are properly selected according to the scattering medium 1 being a measured object and in general, for example, for living tissues, the wavelengths in the near infrared region of approximately 700 to 900 nm are normally used from the relation between transmittance of living tissue and spectral absorption coefficient of absorber to be quantified. The light source 5 can be selected from a variety of sources including light emitting diodes, laser diodes, various pulse lasers, and so on. This light source 5 may be a combination of two or more sources each emitting light of a single wavelength or light of a narrow band, or may be one simultaneously emitting light of two or more wavelengths. The structure of the light guide 3 and wavelength selector 4 is also adequately modified or set according to the structure of the light source 5 as described. The light source may also be one time-sequentially generating light of two or more wavelengths and in this case the wavelength selector 4 can be omitted.

The apparatus illustrated in FIG. 2 is provided with a light guide 6 for photodetection and an input end of the light guide 6 is located at a predetermined position on the surface of the scattering medium 1. A photodetector 7 is optically coupled to an output end of the light guide 6, and the light having propagated with being scattered inside the scattering medium 1 is guided from the position $v_k$ through the light guide 6 to the photodetector 7. The photodetector 7 converts the received signal into a photodetection signal being an electric signal. A signal processing unit 8 is electrically connected to the photodetector 7 and to the light source 5 and this signal processing unit 8 acquires waveform data indicating temporal change of intensity of detected light, based on the photodetection signal. Further, an computation processing unit 9 is electrically connected to the signal processing unit 8 and this computation processing unit 9 performs the operation to compute the mean pathlength and variance of plural photons constituting the detected light, based on the waveform data. The absorption coefficient difference ($\mu_{a2} - \mu_{a1}$) is quantified according to aforementioned Eq. (4.8), based on these mean pathlength, variance, and the ratio of transport scattering coefficients at two wavelengths, and the concentration C of the absorber is further quantified according to aforementioned Eq. (4.9), based on this absorption coefficient difference, or directly.

The light guide 3 for injection of light, wavelength selector 4, and light source 5 described above constitute the light injecting means according to the present invention; the light guide 6 for detection of light and the photodetector 7 the light detecting means according to the present invention; and the signal processing unit 8 the signal processing means according to the present invention, respectively. The computation processing unit 9 is configured with a plurality of functions, which constitute the mean pathlength and variance computing means (or the group delay and second-partial-derivative-of-amplitude computing means) and the absorption coefficient difference calculating means according to the present invention.

It is desirable to form the part except for the light injecting surface coupled to the light guide 3 and except for the light detecting surface coupled to the light guide 6 in the surface of the scattering medium 1, in structure in which light is absorbed inside but blocked outside. In the case wherein light of plural wavelengths simultaneously propagates with being scattered inside the scattering medium 1, a wavelength selecting filter (not illustrated) may be optionally placed between the photodetector 7 and the light guide 6 to carry out the measurement therewith.

Figure 3:
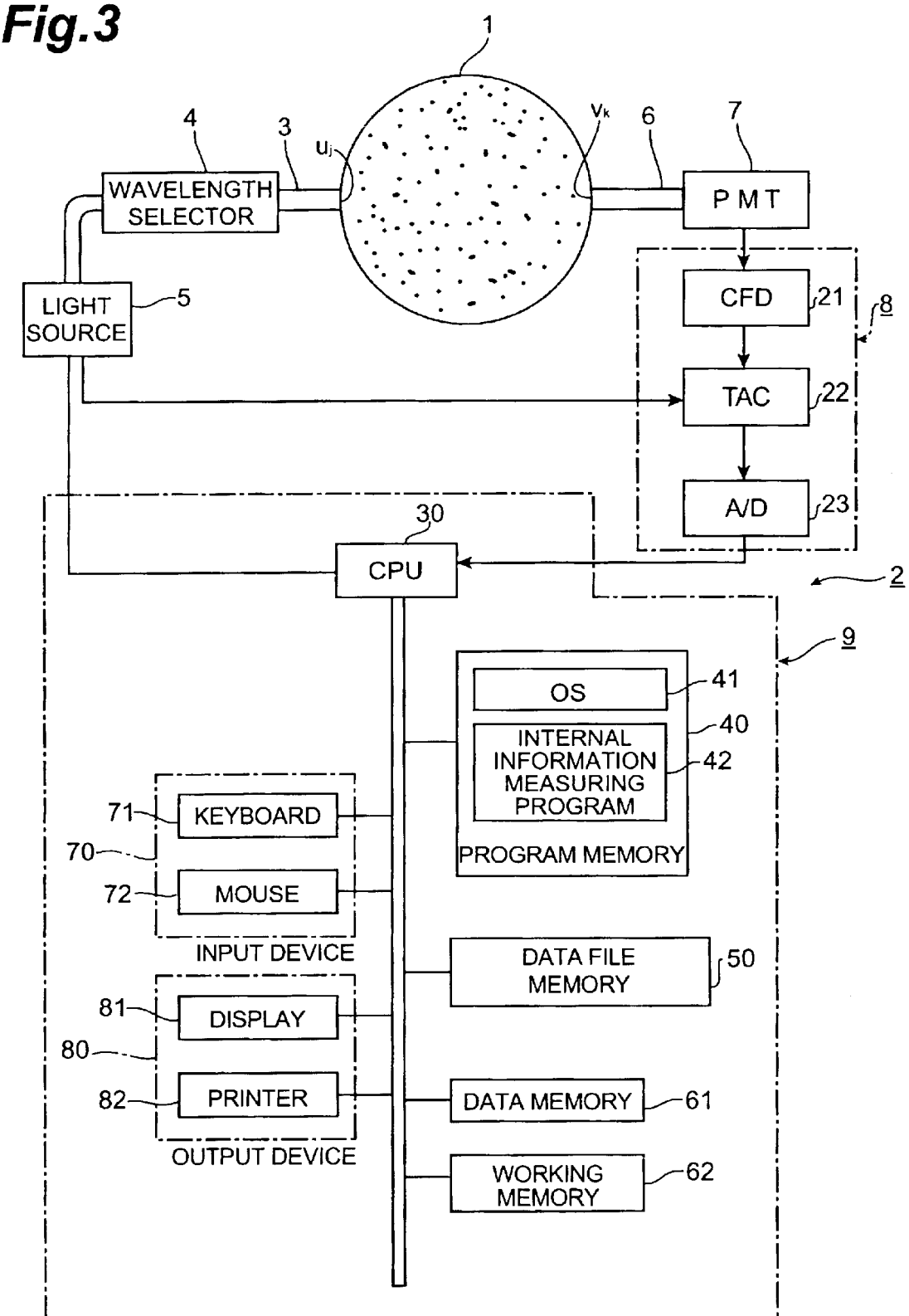
FIG. 3 is a schematic diagram to show an example of preferred specific structure of the apparatus illustrated in FIG. 2.

FIG. 3 shows an example of preferred structure of the photodetector 7, signal processing unit 8, and computation processing unit 9. The setup illustrated in FIG. 3 is a configuration for carrying out a high-speed temporal profile measuring method using a method called so-called time-correlated single photon counting. In this setup example, a photomultiplier tube (PMT) is used as the photodetector 7 and the signal processing unit 8 is composed of a constant fraction discriminator (CFD) 21, a time-to-amplitude converter (TAC) 22, and an AD converter (A/D) 23. Then an output signal from the PMT 7 is guided through CFD 21 to TAC 22 to be converted into an analog voltage corresponding to time. This analog voltage is further converted into a digital signal by the AD converter 23. This digital signal is one corresponding to waveform data indicating temporal change of intensity of detected light.

In the computation processing unit 9 illustrated in FIG. 3, a CPU 30 is electrically connected to the light source 5 and to the signal processing unit 8, the CPU 30 controls the timing of photodetection synchronized with injection of light and others, and the waveform data outputted from the signal processing unit 8 is guided to the CPU 30. This CPU 30 also controls or selects the wavelength of incident light and others. Specific techniques are a technique of injecting light of different wavelengths in time sharing manner and a technique of using light simultaneously containing beams of different wavelengths. Specific wavelength selecting means are, for example, an optical beam switch using a mirror, a wavelength switch using a filter, a light switch using an optical switch, and so on.

The computation processing unit 9 illustrated in FIG. 3 is further provided with a program memory 40 storing an operating system (OS) 41 and an internal information measuring program 42 detailed hereinafter, a data file memory 50 storing various data files, a data memory 61 storing data indicating obtained internal information of the scattering medium, a work memory 62 temporarily saving working data, an input device 70 with a keyboard 71 and a mouse 72 for accepting entry of data, and an output device 80 with a display 81 and a printer 82 for output of obtained data, and these are also controlled by the CPU 30 electrically connected thereto. The above memories may be configured in the form of an internal memory (hard disk) of a computer or a flexible disk.

The data file memory 50 stores various data including the waveform data, mean pathlength, instrumental function (impulse response of the measuring system), variance, ratio of transport scattering coefficients, absorption coefficient difference, etc. obtained by execution of the internal information measuring program 42, and also stores the data of measurement conditions, known values, etc. preliminarily entered by use of the input device 70. Such input data includes the shape of the measured medium, the light injection position, the photodetection position, the source-detector distance, the wavelength of light used in the measurement, the type of measurement (e.g., reflection type or transmission type), the extinction coefficient at a predetermined wavelength of the absorber as a measured object, and so on.

The photodetector 7 can be selected from photodetectors of various kinds, including photodiodes, avalanche photodiodes, PIN photodiodes, etc., as well as the photomultiplier tubes. For selection of the photodetector 7 to be used in the measurement, the necessary condition is that it has spectral sensitivity characteristics capable of detecting re-emission of the wavelengths of the measurement light used. Further, it is preferable to use the photodetector with high sensitivity or with high gain if the photon signal is weak. The source light guide 3 and the detector light guide 6 described above may also be replaced by optical fibers, lenses, or the like.

Next, the measuring method according to the present invention will be described below in detail on the basis of the flowchart of an embodiment thereof illustrated in FIG. 4 (which is a flowchart indicating processing of the internal information measuring program 42 illustrated in FIG. 3).

Figure 4:
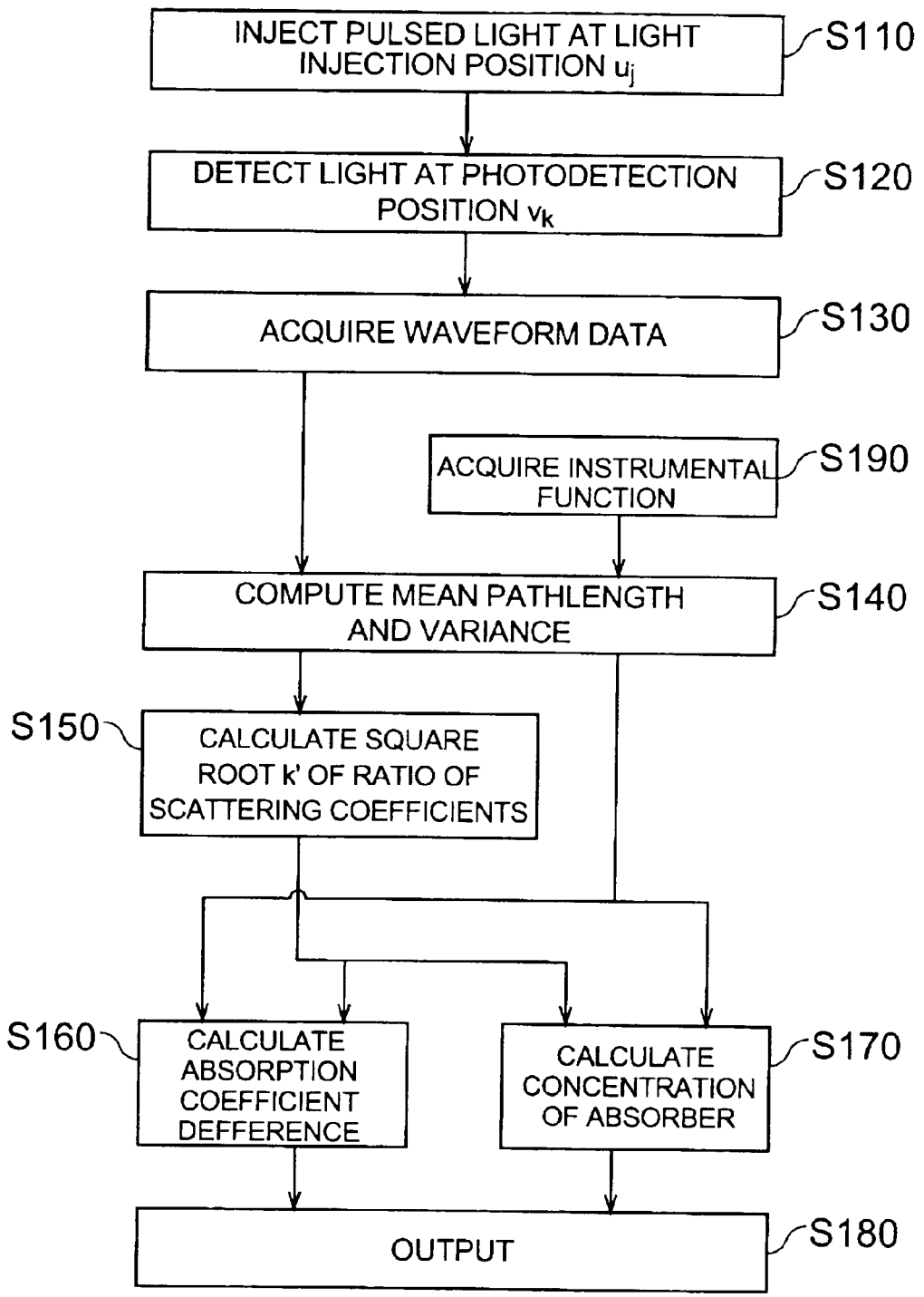
FIG. 4 is a flowchart to show an embodiment of the measuring method of internal information of scattering medium according to the present invention.

In the flowchart illustrated in FIG. 4, the first step is a step of injecting the pulsed light of a predetermined wavelength generated in the light source 5, through the light guide 3 into the scattering medium 1 at the light injection position $u_j$ (S110) and the next step is a step of detecting the light having propagated with being scattered inside the scattering medium 1, by the photodetector 7 through the light guide 6 located at the photodetection position $v_k$ (S120).

Then the photodetector 7 outputs the photodetection signal corresponding to the detected light and the signal processing unit 8 converts it into the waveform data indicating the temporal change of intensity of detected light (S130). The instrumental function (the impulse response of the measuring system) is preliminarily measured (S190) and is stored in the data file memory 50. On this occasion, the instrumental function is measured in such a way that the scattering medium 1 is removed from the structure illustrated in FIG. 3 and the light output end of the light guide 3 and the light input end of the light guide 6 are directly opposed and coupled in contact to each other. Therefore, the instrumental function includes the influence of the pulse width of the light source, the bandwidth of the detecting system, and so on.

Then the mean pathlength L and the variance $\sigma^2$ of plural photons constituting the impulse response are computed, based on the obtained waveform data and instrumental function (S140). The mean pathlength and variance of the impulse response are the sum of the mean pathlengths and the sum of the variances of the measured profile and the instrumental function, respectively, as represented by aforementioned Eqs. (2.8) and (2.10). Since the mean pathlength is expressed by the weighted mean of time-resolved profile as indicated in aforementioned Eq. (1.2b) and the variance by aforementioned (1.3), they can be quickly obtained by computation based on the time-resolved profile, i.e., the waveform data obtained as above with the computer (computation of moment).

Then the square root of the ratio of scattering coefficients, i.e., k' is computed, based on the mean pathlength L and variance 6, in accordance with Eq. (5.6) (S150). Then the absorption coefficient difference of the scattering medium or the concentration of the absorber is calculated based on aforementioned Eq. (4.8) or based on Eq. (4.9), respectively (S160 or S170), and the result of the calculation is outputted (S180).

The above operation to compute the mean pathlength and variance (S140) may also be arranged to obtain the mean pathlength and variance from the impulse response obtained by the deconvolution operation of the waveform data with the instrumental function. In the above operation to compute the square root of the scattering coefficient ratio (S150), it is also possible to use a value preliminarily measured by another method, as described previously.

In the above embodiment, when the light of the predetermined wavelength is pulsed light of n+2 ($\geq 3$, where n is an integer not less than 1) or more wavelengths, it is possible to determine n+1 absorption coefficient differences and quantify concentrations of n+1 absorbers from these values.

Second Embodiment

The present embodiment is an example of application of the present invention to the phase modulation spectroscopy. In this case, the setup of the measuring system is one obtained by replacing the signal processing unit 8 described above and illustrated in FIG. 3, for example, with an computation unit including a lock-in amplifier. The light source 5 emits modulated light of two predetermined wavelengths $\lambda_1$ and/or $\lambda_2$ including three types of modulation frequency components ($\omega_1$, $\omega_2$, $\omega_3$).

Figure 5:
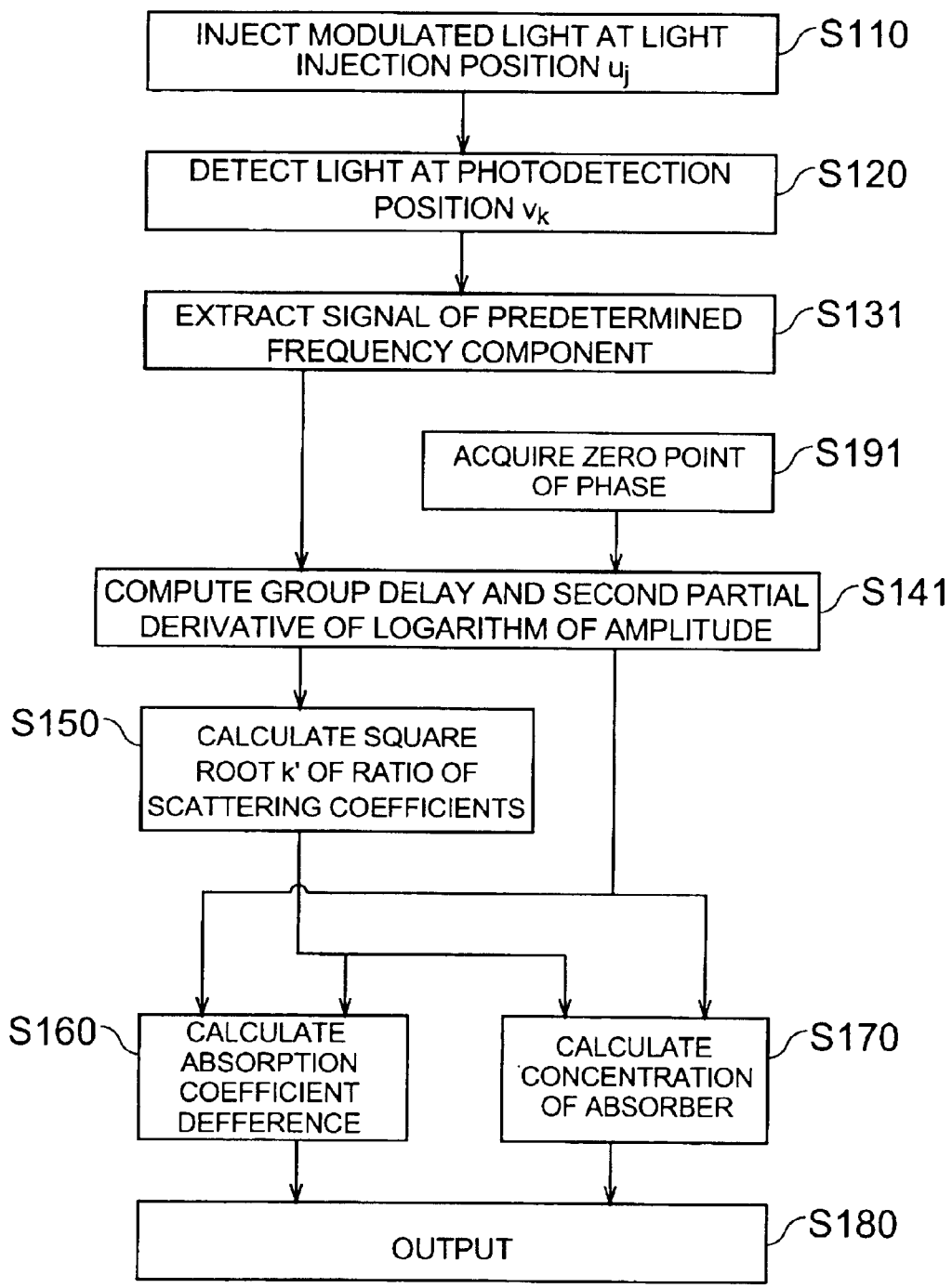
FIG. 5 is a flowchart to show another embodiment of the measuring method of internal information of scattering medium according to the present invention.

FIG. 5 is a flowchart of the embodiment in which the method of the present invention is applied to the phase modulation spectroscopy. In the flowchart illustrated in FIG. 5, the first step is a step of injecting the intensity-modulated light of the predetermined wavelengths generated in the light source 5, through the light guide 3 into the scattering medium 1 at the light injection position $u_j$ (S110) and the next step is a step of detecting the light having propagated with being scattered inside the scattering medium 1, by the photodetector 7 through the light guide 6 located at the photodetection position $v_k$ (S120). Then the photodetection signal corresponding to the detected light is outputted from the photodetector 7 to be supplied to the signal processing unit 8.

The lock-in amplifier included in the signal processing unit 8 extracts signals of the three predetermined frequency components from the modulated light of the wavelengths $\lambda_1$ and $\lambda_2$ described above (S131) and outputs the real parts R, imaginary parts X, amplitudes A, and phase delays $\phi$ stated in Eq. (3.1), about the signals of the three predetermined frequency components. The zero point of the phase is preliminarily acquired (S191). The next step in this embodiment is a step of computing the group delay of plural photons constituting the detected light of the modulation frequency of $\omega_2$, and the second partial derivative of logarithm of amplitude with respect to $\omega$ (which is equal to the partial derivative of the group delay with respect to the absorption coefficient, see Eq. (3.5)), using the amplitudes A, phase delays $\phi$, and three modulation frequencies ($\omega_1$, $\omega_2$, $\omega_3$) of the signals of the three predetermined frequency components against injection of the modulated light of the two predetermined wavelengths (S141).

Then the square root of the ratio of scattering coefficients, i.e., k' is computed based on this group delay and the partial derivative thereof with respect to the absorption coefficient (S150). In this case, the computation is carried out by replacing the mean pathlength L with c times the group delay and replacing the variance $\sigma^2$ with the second partial derivative of logarithm of $c^2$ times the amplitude with respect to $\omega$, in aforementioned Eq. (5.6). Then the absorption coefficient difference of the scattering medium, or the concentration of the absorber is computed based on aforementioned Eq. (4.8) or Eq. (4.9), respectively, (S160 or S170) and the result of the computation is outputted (S180). In these cases, however, the computation is also conducted by replacing the mean pathlength L with c times the group delay and replacing the variance $\sigma^2$ with the second partial derivative of logarithm of $c^2$ times the amplitude with respect to $\omega$.

The above process is arranged to obtain the group delay and the partial derivative thereof with respect to the absorption coefficient, but in the case of $\omega \ll c\mu_a$, the process may also be modified to compute the phase delay and the partial derivative of the phase delay with respect to the absorption coefficient, because the group delay is approximated to the phase delay in that case as described above. In the above operation to compute the square root of the ratio of scattering coefficients (S150), it is also possible to use a value preliminarily measured by another method.

In the above embodiment, when the light of the predetermined wavelengths is pulsed light of n+2 ($\geq 3$, where n is an integer not less than 1) or more wavelengths, it becomes feasible to obtain n+1 absorption coefficient differences and quantify concentrations of n+1 absorbers from these values.

Third Embodiment

Figure 6:
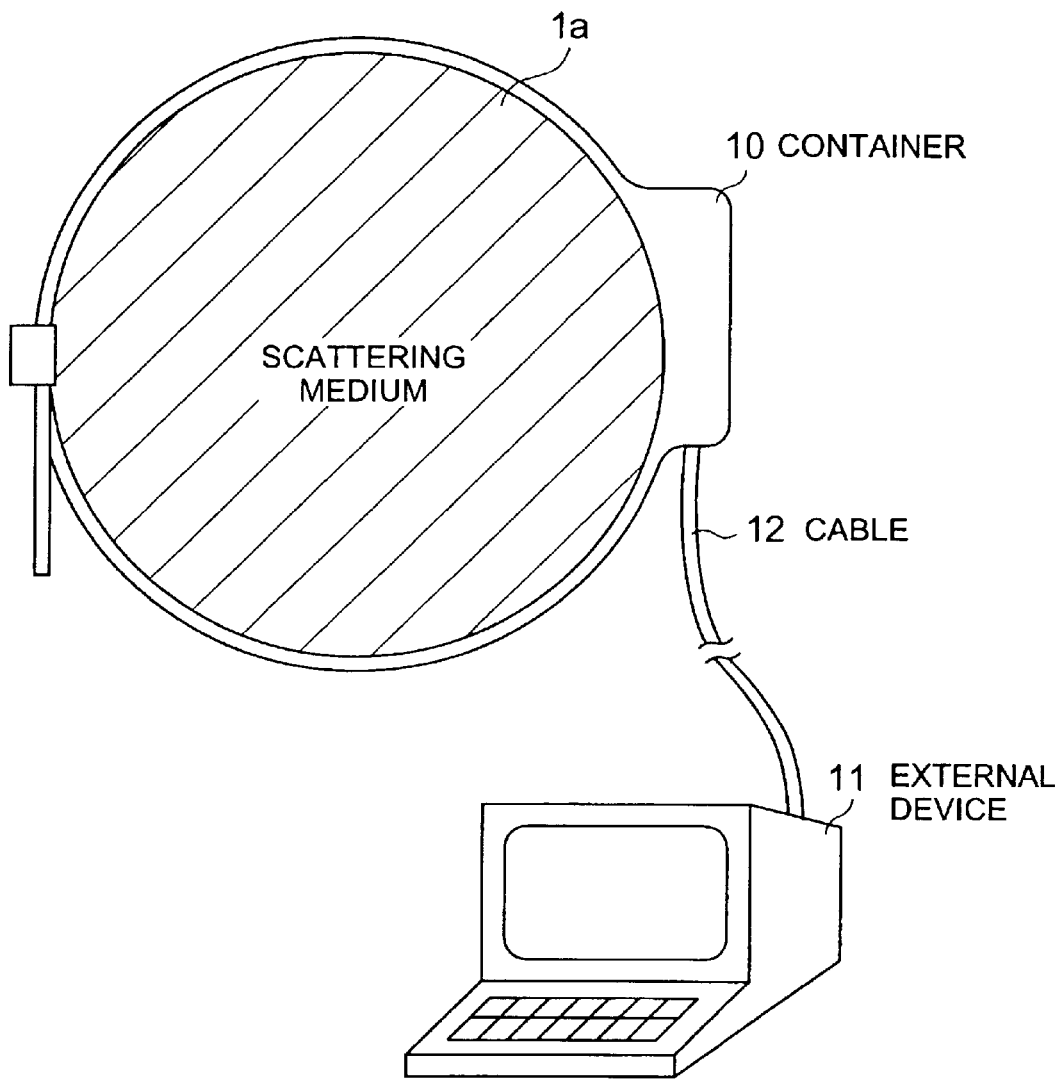
FIG. 6 is a schematic diagram to show another embodiment of the measuring apparatus of internal information of scattering medium according to the present invention.

FIG. 6 shows the third embodiment of the present invention to illustrate a system for measuring or monitoring the concentration of hemoglobin or oxygen saturation of hemoglobin inside a scattering medium such as a human head. This system uses light of three wavelengths, i.e., wavelengths $\lambda_1$, $\lambda_2$, and $\lambda_3$. In this case, the operation principle and structure are the same as in the first embodiment with use of pulsed light and the same as in the second embodiment with use of modulated light. The system of the present embodiment, however, is different in the structure of a container housing the light injecting means and light detecting means from each of the above embodiments.

In the system illustrated in FIG. 6, the light injecting means and light detecting means are housed in the container 10 provided with a fitting band to be mounted on the head 1a like a headband and are connected through a cable 12 to an external device 11 including the signal processing unit 8, the computation processing unit 9, and so on.

Figure 7:
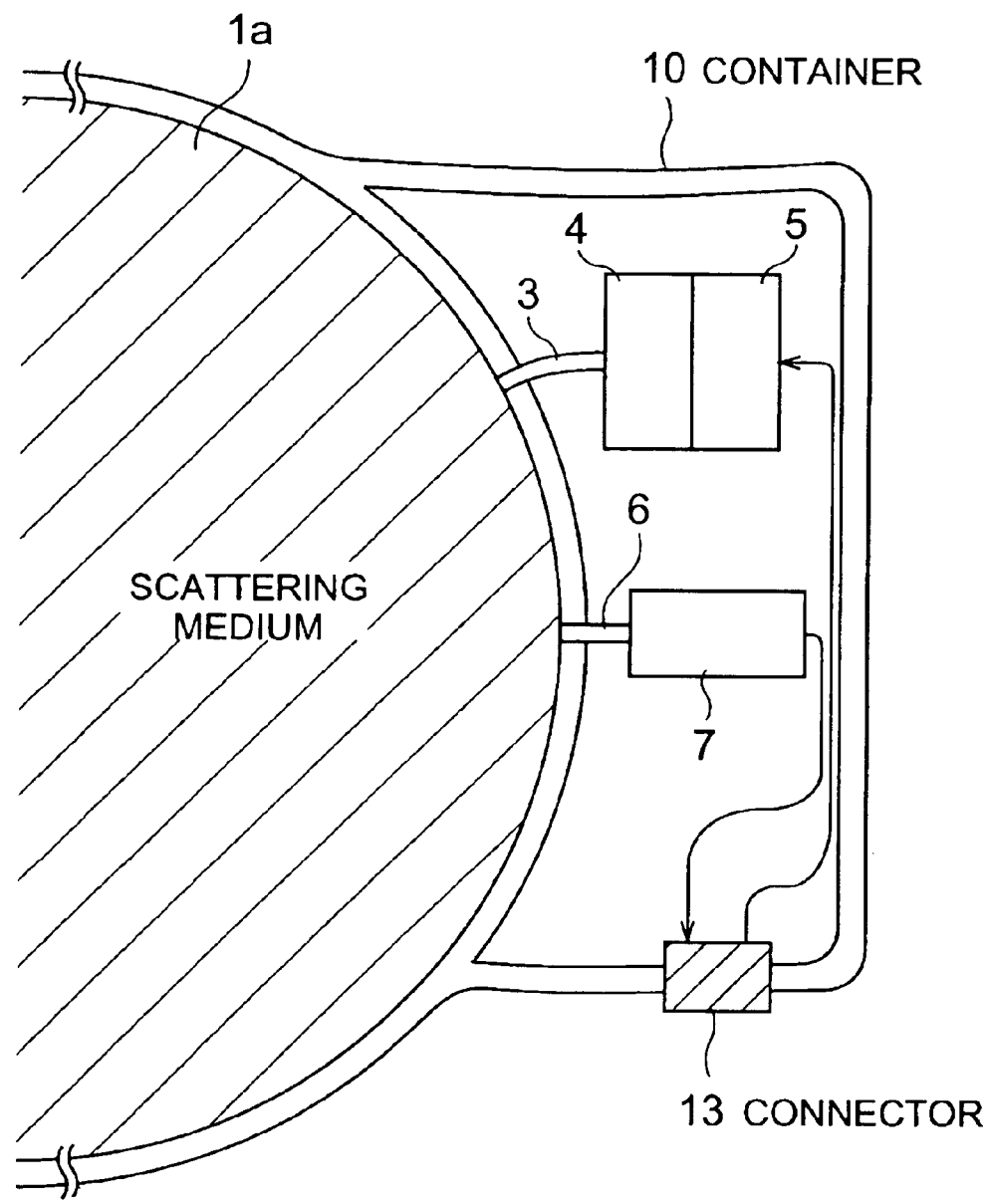
FIG. 7 is a schematic diagram to show an example of preferred specific structure of the apparatus illustrated in FIG. 6.
Figure 8:
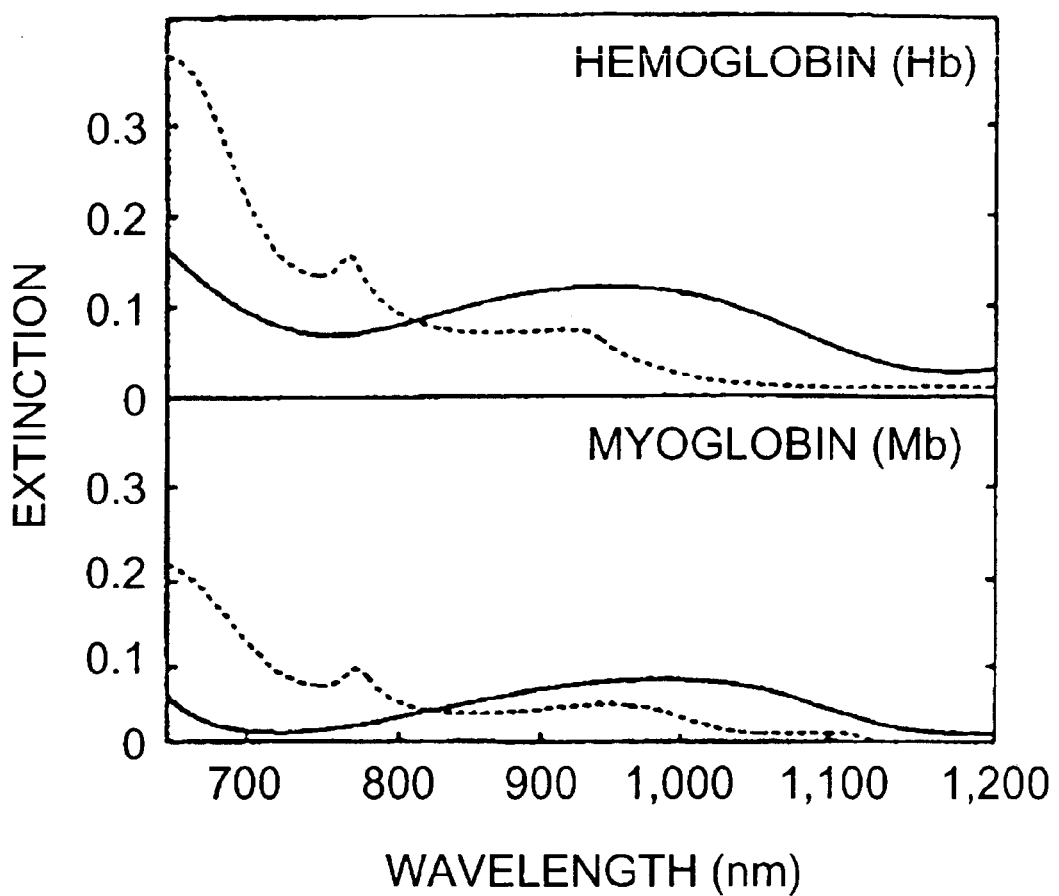
FIG. 8 is a graph to show absorption spectra of hemoglobin.

FIG. 7 shows the details of the container 10. The container 10 incorporates the light source 5, wavelength selector 4, source light guide 3, detector light guide 6, and photodetector 7. The light of the predetermined wavelengths $\lambda_1$, $\lambda_2$, $\lambda_3$ emitted from the light source 5 is subjected to the wavelength selection in the wavelength selector 4 and light of the selected wavelength is guided through the light guide 3 into the head 1a. On this occasion, the predetermined wavelengths $\lambda_1$, $\lambda_2$, and $\lambda_3$ are properly selected with reference to the absorption spectrum of hemoglobin illustrated in FIG. 8.

The above system is constructed in such structure that the cable 12 connects the container 10 incorporating the light injecting means and light detecting means, via a connector 13 with the external device 11 housing the signal processing unit 8 and the computation processing unit 9, but the system may also be constructed so as to connect them with each other by another means such as wireless communication, optical signals, or the like. Such arrangement permits, for example, not only measurement on the bed side or in a state of repose, but also measurement in a state of motion. Besides the head, it is also possible to implement measurement with an object such as the thigh or the like of a marathon runner during a race, for example. Further, if the system is connected to a city cable, an optical cable, or the like, it will also become feasible to implement remote measurement for a person at home from facilities such as hospitals or the like and to apply it to centralized control or the like of patient rooms in the hospitals, for example.

Here let us denote the concentrations and optical constants of hemoglobin as follows.

$C_b$: molar concentration (M) of deoxygenated hemoglobin, $C_o$: molar concentration (M) of oxygenated hemoglobin, $p_1$: molar extinction coefficient (mm$^{-1}$M$^{-1}$) at the wavelength $\lambda_1$ of deoxygenated hemoglobin, $p_2$: molar extinction coefficient (mm$^{-1}$M$^{-1}$) at the wavelength $\lambda_2$ of deoxygenated hemoglobin, $p_3$: molar extinction coefficient (mm$^{-1}$M$^{-1}$) at the wavelength $\lambda_3$ of deoxygenated hemoglobin, $q_1$: molar extinction coefficient (mm$^{-1}$M$^{-1}$) at the wavelength $\lambda_4$ of oxygenated hemoglobin, $q_2$: molar extinction coefficient (mm$^{-1}$M$^{-1}$) at the wavelength $\lambda_5$ of oxygenated hemoglobin, $q_3$: molar extinction coefficient (mm$^{-1}$M$^{-1}$) at the wavelength $\lambda_6$ of oxygenated hemoglobin Then the absorption coefficients at the respective wavelengths are expressed as follows.

$$\mu_{a1}=p_1 C_b + q_1 C_o + a_1$$

$$\mu_{a2}=p_2 C_b + q_2 C_o + a_2$$

$$\mu_{a3}=p_3 C_b + q_3 C_o + a_3 \tag{A1.1}$$

In these equations, $a_1$, $a_2$, and $a_3$ are absorption coefficients of water and the absorbers other than hemoglobin.

Since values actually measured by the method of the present invention are absorption coefficient edifferences, the above equations are rewritten as follows corresponding thereto.

$$\mu_{a2}-\mu_{a1}=(p_2-p_1)C_b+(q_2-q_1)C_o+a_2-a_1$$

$$\mu_{a3}-\mu_{a1}=(p_3-p_1)C_b+(q_3-q_1)C_o+a_3-a_1 \tag{A1.2}$$

Namely, the left sides of the above equations are quantities measured by the method of the present invention. Since these equations are simultaneous equations including two unknowns $C_b$ and $C_o$, the two unknowns $C_b$ and $C_o$ can be determined by solving these simultaneous equations. In this case, as to values of $a_1$, $a_2$, and $a_3$, the wavelengths are normally selected so as to make $a_1 \approx a_2 \approx a_3$. It is also possible to use standard values of living tissues for the values of $a_1$, $a_2$, $a_3$.

According to the above, this embodiment allows us to determine the concentration $C_b$ of deoxygenated hemoglobin, the concentration $C_o$ of oxygenated hemoglobin, the amount of hemoglobin ($C_b+C_o$), and the oxygen saturation $C_o/(C_b+C_o)$.

The above described the preferred embodiments of the present invention, but it is noted that the present invention is by no means limited to the above embodiments, of course.

Specifically, the light injection position and photodetection position are fixed in the above embodiments, but the light injection position and/or the photodetection position may be moved to scan. It can also be contemplated that a plurality of light injection positions and/or photodetection positions are arranged around the scattering medium.

Further, in the above embodiments the scattering characteristics during measurement can be considered to be constant when the measurement is carried out with moving the light injection position and/or the photodetection position relative to one scattering medium, or when the measurement is carried out at a fixed position of a scattering medium before and after change in the concentration of an absorber. In this case, a concentration distribution of an absorber (differences with respect to a reference value) or a concentration change of an absorber (differences with respect to a reference value) can be measured by setting k'=1 in aforementioned Eq. (4.9) and Eq. (4.10). Particularly, the former example is effective, for example, to the measurement in Example 2 (mammography) disclosed in Japanese Patent Application Laid-Open No. H10-73481 by the inventors of the present application.

The present invention will be described in further detail on the basis of examples.

EXAMPLE 1

The present example provides the results of simulation performed for confirming the accuracy of the method of the present invention.

Specifically, Monte Carlo simulation was conducted as to the spectroscopy using the mean pathlength and variance according to the present invention (the MVS method) with variation of absorption coefficient for slablike scattering media (media) having the thickness of 30 mm. Although this Monte Carlo simulation does not present data directly corresponding to data measured by dual-wavelength spectroscopy, it allows simulation of validity of the dual-wavelength spectroscopy, using Monte Carlo data at different concentrations of an absorber. Namely, aforementioned Eq. (4.8) with k'=1 is applied to quantification of the difference between absorption coefficients.

Table 1 and Table 2 present the results of measurement with the source-detector distance of 5 mm in the reflection measurement and Table 3 and Table 4 the results of measurement with the source-detector distance of 30 mm in the reflection measurement. Table 5 and Table 6 present the results of measurement with the source-detector distance of 30 mm (corresponding to the thickness of the medium) in the transmission measurement. The scattering coefficient $\mu'_s=1$ mm$^{-1}$ in all the cases, but the mean cosine of scattering angles is g=0.6 in Tables 1, 3, and 5 and g=0.9 in the Tables 2, 4, and 6.

TABLE 1

| $\mu_a$ | L | σ | $\Delta\mu_a$ | Error (%) | Old-$\Delta\mu_a$ | Error (%) |
|---|---|---|---|---|---|---|
| 0.005 | 26.063 | 31.90 | — | — | — | — |
| 0.01 | 22.98 | 23.15 | 0.0047 | −6 | 0.0053 | 6 |
| 0.02 | 19.30 | 16.17 | 0.0092 | −8 | 0.0111 | 11 |
| 0.03 | 17.23 | 12.91 | 0.0097 | −3 | 0.0114 | 14 |

TABLE 2

| $\mu_a$ | L | σ | $\Delta\mu_a$ | Error (%) | Old-$\Delta\mu_a$ | Error (%) |
|---|---|---|---|---|---|---|
| 0.005 | 26.19 | 31.58 | — | — | — | — |
| 0.01 | 22.62 | 22.91 | 0.0047 | −6 | 0.0053 | 6 |
| 0.02 | 19.00 | 15.99 | 0.0093 | −7 | 0.0111 | 11 |
| 0.03 | 16.98 | 12.76 | 0.0097 | −3 | 0.0116 | 16 |

TABLE 3

| $\mu_a$ | L | σ | $\Delta\mu_a$ | Error (%) | Old-$\Delta\mu_a$ | Error (%) |
|---|---|---|---|---|---|---|
| 0.005 | 283.50 | 137.56 | — | — | — | — |
| 0.01 | 219.51 | 93.43 | 0.0046 | −8 | 0.0046 | −8 |
| 0.02 | 165.16 | 59.20 | 0.0089 | −11 | 0.0102 | 2 |
| 0.03 | 138.77 | 44.44 | 0.0096 | −4 | 0.0110 | 10 |

TABLE 4

| $\mu_a$ | L | σ | $\Delta\mu_a$ | Error (%) | Old-$\Delta\mu_a$ | Error (%) |
|---|---|---|---|---|---|---|
| 0.005 | 284.02 | 137.65 | — | — | — | — |
| 0.01 | 219.75 | 93.32 | 0.0046 | −8 | 0.0046 | −8 |
| 0.02 | 165.44 | 59.03 | 0.0089 | −11 | 0.0104 | 4 |
| 0.03 | 139.39 | 44.40 | 0.0095 | −5 | 0.0110 | 10 |

TABLE 5

| $\mu_a$ | L | σ | $\Delta\mu_a$ | Error (%) | Old-$\Delta\mu_a$ | Error (%) |
|---|---|---|---|---|---|---|
| 0.005 | 231.94 | 110.03 | — | — | — | — |
| 0.01 | 190.39 | 78.01 | 0.0046 | −8 | 0.0056 | 12 |
| 0.02 | 150.92 | 51.83 | 0.0090 | −10 | 0.0117 | 17 |
| 0.03 | 129.03 | 40.63 | 0.0101 | −1 | 0.0104 | 4 |

TABLE 6

| $\mu_a$ | L | σ | $\Delta\mu_a$ | Error (%) | Old-$\Delta\mu_a$ | Error (%) |
|---|---|---|---|---|---|---|
| 0.005 | 232.00 | 110.23 | — | — | — | — |
| 0.01 | 190.29 | 77.74 | 0.0044 | 12 | 0.0057 | 14 |
| 0.02 | 150.39 | 52.05 | 0.0091 | 9 | 0.0113 | 13 |
| 0.03 | 129.18 | 40.22 | 0.0098 | 2 | 0.0116 | 16 |

In each of the tables $\mu_a$ in the left extreme column represents the absorption coefficients of media set on the occasion of Monte Carlo calculation. In the tables $\Delta\mu_a$ in the central part represents the absorption coefficient differences quantified by aforementioned Eq. (4.8), using the mean pathlengths L and variances σ² computed from a set of Monte Carlo data of upper and lower neighbors. However, k'=1. In the tables the right part presents Old-$\Delta\mu_a$ to indicate the absorption coefficient differences obtained by another method for quantifying the ratio of transport scattering coefficients (Eq. (5.3a)) for comparison. From the tables, this Old-$\Delta\mu_a$ shows a tendency of DC biasing in the reflection measurement and a tendency of the slope becoming larger than 1 in the transmission measurement, and $\Delta\mu_a$ obtained by the method according to the present invention demonstrates smaller errors than Old-$\Delta\mu_a$.

The smaller the absorption coefficient $\mu_a$, the larger the change of slope of mean pathlength L against absorption coefficient $\mu_a$ becomes (see FIG. 1). Therefore, there arises the error of linear approximation (equivalent to use of the mean value theorem) used for deriving aforementioned Eq. (1.5), in the small region of the absorption coefficient $\mu_a$. Of course, this error decreases with decrease in the absorption coefficient difference. This tendency is seen in the results of Table 1 to Table 6 and the quantified values in the bottom row show considerably good accuracy. In the spectroscopy of actual living tissues or the like, the difference between absorption coefficients at two wavelengths becomes small just when the absorption coefficient $\mu_a$ is small, as described hereinafter. Since the living tissues involve the absorption of water, absolute values of absorption coefficients also become larger by that degree. Accordingly, these two points largely relax the above error in the spectroscopy of living tissues or the like.

EXAMPLE 2

The present example provides the results of experiments conducted with a simulated phantom in order to confirm the accuracy of the method of the present invention.

The schematic structure of the experimental setup was as illustrated in FIG. 3, and the light source was two picosecond pulse generators that generated picosecond pulses of the respective wavelengths $\lambda_1=782$ nm and $\lambda_2=831$ nm, the repetition rate of 5 MHz, and the pulse width of about 50 ps. These picosecond pulses are injected through an optical switch and an optical attenuator into a GI fiber having the diameter of 200 μm and light emerging from an output end being the other end of the fiber is injected into the phantom being a scattering medium. Output light from the phantom is received by a bundle fiber having the diameter of 5 mm and is measured by the system based on the time-correlated single photon counting method as illustrated in FIG. 3. The instrumental functions at the two wavelengths necessary for the computation of mean pathlength are measured with the light injection and photodetection fibers kept in a closely fitted state.

The phantom used in the experiments was prepared by putting 420 ml of a 1% intralipid solution as a scattering substance into an acrylic vessel (width 120 mm, height 120 mm, and depth 40 mm) and gradually adding greenish brown ink 0.07 ml every time as an absorbing substance to the solution until the total amount of the ink became 0.56 ml, and the transmission measurement was carried out under the condition of the source-detector distance of 40 mm. The actual absorption coefficient of the phantom is the sum of the absorption coefficient of the added ink and the absorption coefficient of water (distilled water). At the wavelengths $\lambda_1=782$ nm and $\lambda_2=831$ nm of the pulsed light used in the measurement, theoretical values of the transport scattering coefficient are 1.0207 and 0.9531, respectively. Therefore, a ratio of them is 1.071 and k'=1/1.035=0.9633. The extinction coefficient of greenish brown ink and the absorption coefficient of distilled water were measured by a spectroscope. Table 7 presents the optical parameters of the phantom in the experiments.

TABLE 7

| Wavelength (nm) | $\lambda_1 = 782$ | $\lambda_2 = 831$ | Difference between or ratio of coefficients at the wavelengths |
|---|---|---|---|
| Absorption coefficient of water (mm$^{-1}$) | $\mu_{w1} = 2.452 \times 10^{-3}$ | $\mu_{w2} = 3.095 \times 10^{-3}$ | $\mu_{w2} - \mu_{w1} = 0.643 \times 10^{-3}$ |
| Extinction coefficient (mm$^{-1}$ · ml$^{-1}$) | $\epsilon_1 = 4.806 \times 10^{-2}$ | $\epsilon_2 = 2.758 \times 10^{-2}$ | $\epsilon_1 - \epsilon_1 = -2.048 \times 10^{-2}$ |
| Transport scattering coefficient (mm$^{-1}$) | $\mu_{s1} = 1.0207$ | $\mu_{s2} = 0.9531$ | $(\mu_{s2}/\mu_{s1})^{1/2} = 0.9633$ |

Table 8 presents values of the mean pathlength and variance of the impulse response calculated from experimental values obtained in the experiments with the phantom carried out under the above conditions.

TABLE 8

| Ink (ml) | $L(\lambda_1)$ (× 10$^2$ mm) | $L(\lambda_2)$ (× 10$^2$ mm) | $\sigma^2(\lambda_1)$ (× 10$^4$ mm) | $\sigma^2(\lambda_2)$ (× 10$^4$ mm) |
|---|---|---|---|---|
| 0.00 | 4.2007 | 3.8468 | 3.5658 | 2.9339 |
| 0.07 | 3.3142 | 3.3683 | 1.6680 | 1.8673 |
| 0.14 | 2.8670 | 3.0533 | 1.0439 | 1.3639 |
| 0.21 | 2.5690 | 2.8141 | 0.7275 | 1.0329 |
| 0.28 | 2.3322 | 2.6051 | 0.5572 | 0.8342 |
| 0.35 | 2.1610 | 2.4412 | 0.4399 | 0.6946 |
| 0.42 | 2.0367 | 2.3369 | 0.3605 | 0.5910 |
| 0.49 | 1.9164 | 2.2304 | 0.2993 | 0.5125 |
| 0.56 | 1.8336 | 2.1266 | 0.2611 | 0.4546 |

Figure 9:
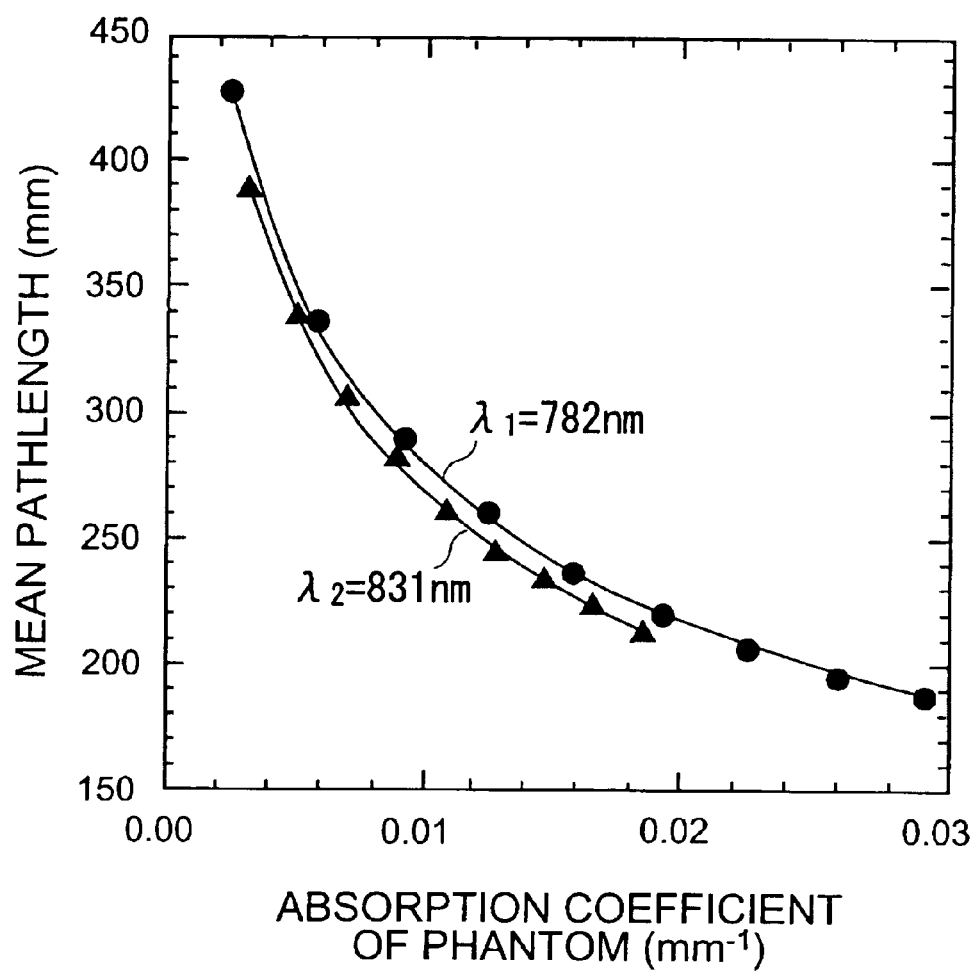
FIG. 9 is a graph to show the relationship between absorption coefficient and mean pathlength of a phantom.

The absorption of water is unignorable in the measurement with the living tissues and living-tissue-simulated liquid phantoms. The extinction coefficient of an absorber differs depending upon wavelengths, and the spectroscopy makes use of this difference. FIG. 9 shows the relation between absorption coefficient and mean pathlength of a phantom. In this relation the absorption coefficients of the phantom were calculated using the absorption coefficient of distilled water actually measured, the quantity of added ink, and the extinction coefficient of ink actually measured. The curves in the figure are the results of fitting in the general form of the following equation indicating the mean photon pathlength obtained by the photon diffusion approximation.

$$L = 1/(a + b\sqrt{\mu_a})$$

It is seen from this FIG. 9 that Eq. (4.6) approximately holds.

Further, it is also seen that, considering the absorption coefficient difference in a set of data used in the spectroscopy in the figure, i.e., in a set of data at the same quantity of added ink, this difference increases with increase in the absorption coefficient of the phantom and the difference also becomes smaller with decrease in the absorption coefficient of the phantom. This relation generally holds for the spectroscopy of living tissues or the like. The linear approximation was used for deriving Eq. (1.5) being the fundamental equation of the MVS method. Since the curvature of mean pathlength and the absorption coefficient difference are just in the relation of one increasing with decrease of the other, as illustrated in FIG. 9, it is seen that the linear approximation holds with small error throughout the entire region of change of the absorption coefficient.

Concentrations C of the absorber quantified by the experiments are presented in Table 9. For comparison's sake, Table 9 also presents the results by the method using a fixed value for the ratio k' (k'=0.9663, which is a theoretical value), the results on the assumption that the transport scattering coefficient has no wavelength dependence (k'=1), and the results by use of an average of the ratios of transport scattering coefficients obtained by the experiments (k'=0.9681). It is apparent from this table that the errors are naturally large on the assumption that the transport scattering coefficient has no wavelength dependence (k'=1) and that the method according to the present invention assures excellent accuracy as against the other methods.

As compared with the results by use of the average of the ratios gained by the experiments (k'=0.9681), the results with k' obtained in each measurement show smaller errors, and this is conceivably because the influence of noise in each measurement is canceled out in the process of operation.

TABLE 9

| | Method of the invention | | | k' = 0.9663 | | k' = 1 | | k' = 0.9681 | |
|---|---|---|---|---|---|---|---|---|---|
| Ink (ml) | k' | C (ml) | Error (%) | $C_{k'2}$ (ml) | Error (%) | $C_{k'1}$ (ml) | Error (%) | $C_{k'3}$ (ml) | Error (%) |
| 0.00 | 0.9646 | -0.000 | — | -0.001 | — | -0.022 | — | -0.002 | — |
| 0.07 | 0.9737 | 0.071 | 1.4 | 0.078 | 11.4 | 0.046 | -34 | 0.076 | 8.5 |
| 0.14 | 0.9697 | 0.144 | 2.9 | 0.148 | 5.7 | 0.107 | -24 | 0.146 | 4.3 |
| 0.21 | 0.9709 | 0.211 | 0.5 | 0.218 | 3.8 | 0.168 | -20 | 0.216 | 2.9 |
| 0.28 | 0.9738 | 0.269 | -3.9 | 0.282 | 0.7 | 0.223 | -20 | 0.279 | -0.4 |
| 0.35 | 0.9652 | 0.342 | -2.3 | 0.340 | -2.9 | 0.273 | -22 | 0.337 | -3.7 |
| 0.42 | 0.9693 | 0.409 | -2.6 | 0.416 | -1.0 | 0.340 | -19 | 0.412 | -1.9 |
| 0.49 | 0.9690 | 0.487 | -0.6 | 0.494 | 0.8 | 0.410 | -16 | 0.489 | -0.2 |
| 0.56 | 0.9566 | 0.549 | -2.0 | 0.520 | -7.1 | 0.432 | -23 | 0.518 | -7.5 |

INDUSTRIAL APPLICABILITY

The measuring methods and apparatus of internal information of scattering medium according to the present invention are applicable to measurement of the absorption coefficient of the scattering medium and the concentration of the absorber, as measuring methods and apparatus of internal information of scattering medium capable of measurement with higher accuracy and at higher speed than the conventional measuring methods based on the MBL law. Particularly, the measuring methods and apparatus according to the present invention make use of the mean pathlength and variance, or physical quantities equivalent thereto, but do not make use of information of the absolute value of light intensity or the ratio thereof. Accordingly, they are useful in that a solution is given to the difficult problem in practical use; quantifying or estimating the absolute value of quantity of light injected into the medium.

Such methods make real-time measurement feasible and also possess the great feature that the measurement can be conducted independent of the shape and boundary conditions, the size of the medium, the scattering characteristics, the source-detector distance, the measurement mode of either transmission or reflection, and so on. From the above, the measuring methods and apparatus of internal information of scattering medium according to the present invention are expected to be commonly applied to apparatus for simply measuring various physiological substances in living tissues on a noninvasive and real-time basis.

What is claimed is:

1. A measuring method of internal information of a scattering medium, comprising:

a light injecting step of injecting pulsed light of two or more predetermined wavelengths into a scattering medium at a light injection position;

a light detecting step of detecting the light of said two or more predetermined wavelengths having propagated inside said scattering medium, at a photodetection position to acquire a photodetection signal;

a signal processing step of acquiring waveform data indicating a temporal change of intensity of the detected light, based on said photodetection signal;

a mean pathlength and variance computing step of performing an operation to compute a mean pathlength of plural photons composing said detected light, and a variance, based on said waveform data; and an absorption coefficient difference calculating step of calculating a difference between absorption coefficients at said predetermined wavelengths, based on a predetermined relation holding among said mean pathlength, said variance, and the difference between the absorption coefficients at said two or more predetermined wavelengths.

2. A measuring method of internal information of a scattering medium according to claim 1, wherein said absorption coefficient difference calculating step comprises a step of further calculating a concentration of an absorber, based on said difference between the absorption coefficients at said two or more predetermined wavelengths and a difference between extinction coefficients of the absorber thereat.

3. A measuring method of internal information of a scattering medium according to claim 1, wherein said operation carried out in said mean pathlength and variance computing step is an operation executed using a mean pathlength and a variance of said photodetection signal and a mean pathlength and a variance of an instrumental function.

4. A measuring method of internal information of a scattering medium according to claim 1, wherein said predetermined relation used in said absorption coefficient difference calculating step is a relation among said mean pathlength, said variance, and said difference between the absorption coefficients at said two or more predetermined wavelengths derived from the Microscopic Beer-Lambert law.

5. A measuring method of internal information of a scattering medium according to claim 1, wherein said pulsed light used in said light injecting step is said pulsed light of said predetermined wavelengths of n+1 kinds (where n is an integer not less than 1), said photodetection signal detected in said light detecting step is said photodetection signals of n+1 kinds, said waveform data acquired in said signal processing step is said waveform data of n+1 kinds, said mean pathlength and said variance computed in said mean pathlength and variance computing step are said mean pathlengths and said variances of n+1 kinds, and said difference between the absorption coefficients calculated in said absorption coefficient difference calculating step is said differences of n kinds between the absorption coefficients at said predetermined wavelengths of n+1 kinds.

6. A measuring method of internal information of a scattering medium according to claim 5, wherein said absorption coefficient difference calculating step comprises a step of further calculating concentrations of absorbers of n kinds, based on said differences of n kinds between the absorption coefficients at said predetermined wavelengths of n+1 kinds and differences between extinction coefficients of the absorbers of n kinds thereat.

7. A measuring method of internal information of a scattering medium, comprising:

a light injecting step of injecting modulated light of two or more predetermined wavelengths modulated at a predetermined frequency, into a scattering medium at a light injection position;

a light detecting step of detecting said light of said two or more predetermined wavelengths having propagated inside said scattering medium, at a photodetection position to acquire a photodetection signal;

a signal processing step of extracting a signal of said predetermined frequency component from said photodetection signal;

a group delay and second-partial-derivative-of-logarithm-of-amplitude computing step of computing a group delay of the signal of said predetermined frequency component and a second partial derivative of logarithm of amplitude with respect to the modulation frequency, based on said signal of the predetermined frequency component; and an absorption coefficient difference calculating step of calculating a difference between absorption coefficients at said predetermined wavelengths, based on a predetermined relation holding among said group delay, said second partial derivative of logarithm of amplitude with respect to the modulation frequency, and the difference between the absorption coefficients at said two or more predetermined wavelengths.

8. A measuring method of internal information of a scattering medium according to claim 7, wherein said absorption coefficient difference calculating step comprises a step of further calculating a concentration of an absorber, based on said difference between the absorption coefficients at said two or more predetermined wavelengths and a difference between extinction coefficients of the absorber thereat.

9. A measuring method of internal information of a scattering medium according to claim 7, wherein said predetermined relation used in said absorption coefficient difference calculating step is a relation among said group delay, said second partial derivative of logarithm of amplitude with respect to the modulation frequency, and the difference between the absorption coefficients at said two or more predetermined wavelengths derived from the Microscopic Beer-Lambert law.

10. A measuring method of internal information of a scattering medium according to claim 7, wherein said modulated light used in said light injecting step is said modulated light of said predetermined wavelengths of n+1 kinds (where n is an integer not less than 1), said photodetection signal detected in said light detecting step is said photodetection signals of n+1 kinds, said signal of the predetermined frequency component extracted in said signal processing step is said signals of predetermined frequency components of n +1 kinds, said group delay and said second partial derivative of logarithm of amplitude with respect to the modulation frequency computed in said group delay and second-partial-derivative-of-logarithm-of-amplitude computing step are said group delays and said second partial derivatives of logarithm of amplitude with respect to the modulation frequency of n+1 kinds, and said difference between the absorption coefficients calculated in said absorption coefficient difference calculating step is said differences of n kinds between the absorption coefficients at said predetermined wavelengths of n+1 kinds.

11. A measuring method of internal information of a scattering medium according to claim 10, wherein said absorption coefficient difference calculating step comprises a step of further calculating concentrations of absorbers of n kinds, based on said differences of n kinds between the absorption coefficients at said predetermined wavelengths of n+1 kinds and differences between extinction coefficients of the absorbers of n kinds thereat.

12. A measuring apparatus of internal information of a scattering medium, comprising:

light injecting means for injecting pulsed light of two or more predetermined wavelengths into a scattering medium at a light injection position;

light detecting means for detecting the light of said two or more predetermined wavelengths having propagated inside said scattering medium, at a photodetection position to acquire a photodetection signal;

signal processing means for acquiring waveform data indicating a temporal change of intensity of the detected light, based on said photodetection signal;

mean pathlength and variance computing means for performing an operation to compute a mean pathlength of plural photons composing said detected light, and a variance, based on said waveform data; and absorption coefficient difference calculating means for calculating a difference between absorption coefficients at said predetermined wavelengths, based on a predetermined relation holding among said mean pathlength, said variance, and the difference between the absorption coefficients at said two or more predetermined wavelengths.

13. A measuring apparatus of internal information of a scattering medium according to claim 12, wherein said absorption coefficient difference calculating means further calculates a concentration of an absorber, based on said difference between the absorption coefficients at said two or more predetermined wavelengths and a difference between extinction coefficients of the absorber thereat.

14. A measuring apparatus of internal information of a scattering medium according to claim 12, wherein said operation carried out by said mean pathlength and variance computing means is an operation executed using a mean pathlength and a variance of said photodetection signal and a mean pathlength and a variance of an instrumental function.

15. A measuring apparatus of internal information of a scattering medium according to claim 12, wherein said predetermined relation used in said absorption coefficient difference calculating means is a relation among said mean pathlength, said variance, and said difference between the absorption coefficients at said two or more predetermined wavelengths derived from the Microscopic Beer-Lambert law.

16. A measuring apparatus of internal information of a scattering medium according to claim 12, wherein said pulsed light used in said light injecting means is said pulsed light of said predetermined wavelengths of n+1 kinds (where n is an integer not less than 1), said photodetection signal detected by said light detecting means is said photodetection signals of n+1 kinds, said waveform data acquired by said signal processing means is said waveform data of n+1 kinds, said mean pathlength and said variance computed by said mean pathlength and variance computing means are said mean pathlengths and said variances of n+1 kinds, and said difference between the absorption coefficients calculated by said absorption coefficient difference calculating means is said differences of n kinds between the absorption coefficients at said predetermined wavelengths of n+1 kinds.

17. A measuring apparatus of internal information of a scattering medium according to claim 16, wherein said absorption coefficient difference calculating means further calculates concentrations of absorbers of n kinds, based on said differences of n kinds between the absorption coefficients at said predetermined wavelengths of n+1 kinds and differences between extinction coefficients of the absorbers of n kinds thereat.

18. A measuring apparatus of internal information of a scattering medium, comprising:

light injecting means for injecting modulated light of two or more predetermined wavelengths modulated at a predetermined frequency, into a scattering medium at a light injection position;

light detecting means for detecting said light of said two or more predetermined wavelengths having propagated inside said scattering medium, at a photodetection position to acquire a photodetection signal;

signal processing means for extracting a signal of said predetermined frequency component from said photodetection signal;

group delay and second-partial-derivative-of-logarithm-of-amplitude computing means for computing a group delay of the signal of said predetermined frequency component and a second partial derivative of logarithm of amplitude with respect to the modulation frequency, based on said signal of the predetermined frequency component; and absorption coefficient difference calculating means for calculating a difference between absorption coefficients at said predetermined wavelengths, based on a predetermined relation holding among said group delay, said second partial derivative of logarithm of amplitude with respect to the modulation frequency, and the difference between the absorption coefficients at said two or more predetermined wavelengths.

19. A measuring apparatus of internal information of a scattering medium according to claim 18, wherein said absorption coefficient difference calculating means further calculates a concentration of an absorber, based on said difference between the absorption coefficients at said two or more predetermined wavelengths and a difference between extinction coefficients of the absorber thereat.

20. A measuring apparatus of internal information of a scattering medium according to claim 18, wherein said predetermined relation used in said absorption coefficient difference calculating means is a relation among said group delay, said second partial derivative of logarithm of amplitude with respect to the modulation frequency, and the difference between the absorption coefficients at said two or more predetermined wavelengths derived from the Microscopic Beer-Lambert law.

21. A measuring apparatus of internal information of a scattering medium according to claim 18, wherein said modulated light used in said light injecting means is said modulated light of said predetermined wavelengths of n+1 kinds (where n is an integer not less than 1), said photodetection signal detected by said light detecting means is said photodetection signals of n+1 kinds, said signal of the predetermined frequency component extracted by said signal processing means is said signals of predetermined frequency components of n+1 kinds, said group delay and said second partial derivative of logarithm of amplitude with respect to the modulation frequency computed by said group delay and second-partial-derivative-of-logarithm-of-amplitude computing means are said group delays and said second partial derivatives of logarithm of amplitude with respect to the modulation frequency of n+1 kinds, and said difference between the absorption coefficients calculated by said absorption coefficient difference calculating means is said differences of n kinds between the absorption coefficients at said predetermined wavelengths of n+1 kinds.

22. A measuring apparatus of internal information of a scattering medium according to claim 21, wherein said absorption coefficient difference calculating means further calculates concentrations of absorbers of n kinds, based on said differences of n kinds between the absorption coefficients at said predetermined wavelengths of n+1 kinds and differences between extinction coefficients of the absorbers of n kinds thereat.

* * * * *